US012186217B2

(12) United States Patent
Einav et al.

(10) Patent No.: US 12,186,217 B2
(45) Date of Patent: Jan. 7, 2025

(54) DEPLOYMENT OF MULTIPLE BILIARY STENTS

(71) Applicant: ENDO GI MEDICAL LTD., Nazareth (IL)

(72) Inventors: Elad Einav, Salit (IL); Ronny Barak, Tel Aviv (IL); Omri Naveh, Ramat Yishay (IL)

(73) Assignee: ENDO GI MEDICAL LTD., Nazareth (IL)

( * ) Notice: Subject to any disclaimer, the term of this patent is extended or adjusted under 35 U.S.C. 154(b) by 968 days.

(21) Appl. No.: 17/254,865

(22) PCT Filed: Jun. 27, 2019

(86) PCT No.: PCT/IL2019/050713
§ 371 (c)(1),
(2) Date: Dec. 22, 2020

(87) PCT Pub. No.: WO2020/003316
PCT Pub. Date: Jan. 2, 2020

(65) Prior Publication Data
US 2021/0259867 A1 Aug. 26, 2021

Related U.S. Application Data

(63) Continuation-in-part of application No. 16/064,843, filed as application No. PCT/IL2016/051368 on Dec. 22, 2016, now Pat. No. 11,154,411.
(Continued)

(30) Foreign Application Priority Data

Dec. 22, 2015 (GB) ...................................... 1522683

(51) Int. Cl.
*A61F 2/04* (2013.01)
*A61F 2/95* (2013.01)
(Continued)

(52) U.S. Cl.
CPC .................. *A61F 2/97* (2013.01); *A61F 2/04* (2013.01); *A61F 2/966* (2013.01); *A61F 2002/041* (2013.01); *A61F 2002/9511* (2013.01)

(58) Field of Classification Search
CPC .... A61F 2/04; A61F 2/95; A61F 2/954; A61F 2/966; A61F 2/97; A61F 2002/041;
(Continued)

(56) References Cited

U.S. PATENT DOCUMENTS 4,781,690 A 11/1988 Ishida
4,874,374 A 10/1989 Kousai
(Continued)

FOREIGN PATENT DOCUMENTS

AU 2020201370 A1 3/2020
CA 2597424 A1 8/2007
(Continued)

OTHER PUBLICATIONS

International Search Report for PCT/IL2019/050713 dated Oct. 4, 2019.
(Continued)

*Primary Examiner* — Diane D Yabut
(74) *Attorney, Agent, or Firm* — Marc Van Dyke; Momentum IP

(57) ABSTRACT

A guide tube (220) has a guidewire-engaging portion (222) at a distal portion (260) thereof, a first stent (54) surrounding the guide tube, advanceable together with the guide tube into a subject's lumen, a guidewire (12) arranged (i) entering the guide tube from a distal-end (320) opening thereof, (ii) disposed in the guidewire-engaging portion, and (iii) passing out of the guide tube proximally to the guidewire-engaging portion, and a second stent (54), proximal to the first stent, surrounding a proximal portion (240) of the guide tube and
(Continued)

the guidewire. The first stent is slidably deployable off the distal end of the guide tube upon the guidewire having laterally exited the guidewire-engaging portion, and the second stent is slidably deployable off the distal end of the guide tube subsequently to deployment of the first stent, without the guidewire having been moved proximally. Other applications are also described.

5 Claims, 21 Drawing Sheets

Related U.S. Application Data

(60) Provisional application No. 62/691,329, filed on Jun. 28, 2018.

(51) Int. Cl.
  *A61F 2/966* (2013.01)
  *A61F 2/97* (2013.01)

(58) Field of Classification Search
  CPC ........ A61F 2002/826; A61F 2002/9505; A61F 2002/9511
  See application file for complete search history.

(56) References Cited

U.S. PATENT DOCUMENTS

| | | | |
|---|---|---|---|
| 4,913,141 A * | 4/1990 | Hillstead | A61F 2/88 623/1.11 |
| 5,669,924 A | 9/1997 | Shaknovich | |
| 6,299,595 B1 | 10/2001 | Dutta | |
| 6,346,093 B1 | 2/2002 | Allman | |
| 7,691,125 B2 | 4/2010 | Ducharme | |
| 8,690,756 B2 | 4/2014 | Deal | |
| 8,955,520 B2 | 2/2015 | Devereux | |
| 9,095,466 B2 | 8/2015 | Norris | |
| 9,402,755 B2 | 8/2016 | Norris | |
| 11,154,411 B2 | 10/2021 | Einav | |
| 11,744,694 B2 | 9/2023 | Naveh | |
| 2001/0044622 A1 | 11/2001 | Vardi | |
| 2004/0215331 A1 * | 10/2004 | Chew | A61F 2/958 623/1.21 |
| 2005/0085891 A1 | 4/2005 | Goto | |
| 2005/0125050 A1 | 6/2005 | Carter | |
| 2005/0143770 A1 | 6/2005 | Carter | |
| 2005/0222603 A1 | 10/2005 | Andreas | |
| 2007/0293929 A1 * | 12/2007 | Aoba | A61F 2/95 623/1.11 |
| 2009/0171427 A1 | 7/2009 | Melsheimer | |
| 2010/0121426 A1 | 5/2010 | Howell | |
| 2011/0087234 A1 * | 4/2011 | Ayala | A61M 25/0662 606/108 |
| 2013/0030416 A1 | 1/2013 | Fernandes | |
| 2014/0188210 A1 | 7/2014 | Beard | |
| 2015/0011834 A1 | 1/2015 | Ayala | |
| 2021/0196444 A1 | 7/2021 | Naveh | |
| 2021/0259867 A1 | 8/2021 | Einav | |

FOREIGN PATENT DOCUMENTS

| | | |
|---|---|---|
| EP | 1867305 A2 | 12/2007 |
| EP | 2278939 B1 | 4/2021 |
| JP | 2012152344 A | 8/2012 |
| JP | 5687216 B2 | 3/2015 |
| WO | 2005/011530 A1 | 2/2005 |
| WO | 2005/011791 A2 | 2/2005 |
| WO | 2006/015323 A2 | 2/2006 |
| WO | 2017/109783 A1 | 6/2017 |
| WO | 2020/003316 A1 | 1/2020 |

OTHER PUBLICATIONS

Machine Translation (Google Patents) for JP2012152344 published on Aug. 16, 2012 Terumo Corp.
Machine Translation (Google Patents) for JP201252344 published Aug. 16, 2012 Terumo Corp.
Machine Translation (Google Patents) for JP5687216 published on Mar. 18, 2015 Bolton Medical Inc.
Ternational Search Report for PCT/IL2016/051368 dated Oct. 2, 2017.
Written Opinion for PCT/IL2016/051368 dated Oct. 2, 2017.
Written Opinion for PCT/IL2019/050713 dated Oct. 4, 2019.

* cited by examiner

DEPLOYMENT OF MULTIPLE BILIARY STENTS

CROSS-REFERENCES TO RELATED APPLICATIONS

The present application claims the priority of U.S. 62/691,329 to Einav et al., filed Jun. 28, 2018, entitled, "Deployment of multiple biliary stents."

The present application is a continuation-in-part of U.S. patent application Ser. No. 16/064,843, which is the national phase of PCT application No. PCT/IL2016/051368 to Einav, entitled "Deployment of Multiple Biliary Stents," filed Dec. 22, 2016, published as WO 2017/109783, which claims priority of GB Patent Application No. 1522683.0 to Einav, entitled "Deployment of Multiple Biliary Stents," filed Dec. 22, 2015.

Each of the above patent applications is incorporated herein by reference.

FIELD OF THE INVENTION

Embodiments of the present invention relate generally to medical devices and more particularly to methods and apparatus for deploying multiple stents in a lumen of a subject.

BACKGROUND

Stents are typically deployed within a lumen of a body of a subject for various reasons. In some cases, a stent is deployed within a lumen in order to widen a narrowed section of the lumen. For example, insertion of a biliary stent into a bile duct is used to treat obstructions and strictures that occur in the bile duct. There are several conditions, malignant or benign, that can cause strictures of the bile duct. Pancreatic cancer is a common malignant cause of strictures of the bile duct. Noncancerous causes of bile duct stricture may include injury to the bile duct that occurs during surgery for gallbladder removal, and pancreatitis.

A biliary stent is typically a tube-like structure that is used to support a narrowed part of the bile duct and inhibit the reformation of the stricture.

SUMMARY OF THE INVENTION

In accordance with some applications of the present invention, apparatus and methods are provided for deployment of more than one stent (e.g., two stents) within a lumen of a subject. For example, two or more stents are deployed within a common bile duct of a subject in order to treat biliary strictures and obstructions. Typically, the two or more stents, e.g., two, three or four stents, are deployed alongside each other within the common bile duct to facilitate relieving of the biliary stricture. Typically, a guide tube is used to deploy the stents (e.g., a first and a second stent) in the lumen of the subject. In this context, in the specification and in the claims, "proximal" means closer to the orifice through which the guide tube or stent is originally placed into the body, and "distal" means further from this orifice.

For some applications, the guide tube is shaped to define a guidewire-engaging portion, e.g., a slit, extending proximally along the wall of the guide tube, from the distal end of the guide tube. A proximal end of the slit is typically located distally to the proximal end of the guide tube. Additionally, the guide tube is shaped to define a hole through a wall of the guide tube, the hole being located proximally to the proximal end of the guidewire-engaging portion and distally to the proximal end of the guide tube. Typically, a proximal end of the slit is located distally to the hole.

During delivery into the lumen of the subject, the first stent surrounds the guide tube and is advanced together with the guide tube into the lumen of the subject. Typically, the first stent is disposed along the guide tube such that, prior to insertion into the subject's body, a proximal end of the first stent is disposed distally to the hole in the wall of the guide tube while a distal end of the first stent is disposed proximally to the guidewire-engaging portion. When positioned at a desired site within the lumen of the subject, the first stent is slidably deployed from, i.e., advanced off of, the distal end of the guide tube and deployed within the lumen.

Also prior to insertion into the subject's body, the second stent is disposed proximal to the first stent, surrounding a proximal portion of the guide tube. (The proximal portion of the guide tube is called the "proximal portion" because it is proximal to the more distal portion of the guide tube, around which the first stent is disposed. The proximal portion of the guide tube, as well as the second stent surrounding the proximal portion of the guide tube, is introduced into the subject's body, as described herein.) The second stent is shaped and sized to be advanced over the guide tube and off of the distal end of the guide tube into the lumen of the subject. The second stent is placed alongside the first stent subsequently to deployment of the first stent off of the distal end of the guide tube.

In accordance with some applications of the present invention, the first and second stents are delivered to the lumen of the subject without removing the guide tube or a guidewire used during the procedure from the body of the subject following deployment of the first stent and prior to deploying the second stent. As provided by some applications of the present invention, the first and second stents are both pre-mounted onto the guide tube and advanced into the subject's body in one advancement procedure, to be deployed subsequently within the lumen of the subject, as described herein.

There is therefore provided in accordance with some applications of the present invention, apparatus, including:
- a guide tube shaped to define (a) a guidewire-engaging portion at a distal portion of the guide tube, a proximal end of the guidewire-engaging portion being located distally to a proximal end of the guide tube, (b) a hole in a wall of the guide tube, the hole being located proximally to the proximal end of the guidewire-engaging portion and distally to a proximal end of the guide tube;
- a first stent surrounding the guide tube so as to be advanceable together with the guide tube into a lumen of a subject, the first stent being slidable along the guide tube such that a proximal end of the first stent is disposable distally to the hole while a distal end of the first stent is disposed proximally to the guidewire-engaging portion, the first stent being slidably deployable off of the distal end of the guide tube; and
- a second stent, proximal to the first stent, surrounding a proximal portion of the guide tube, and shaped and sized to be advanceable along the guide tube and deployable off of the distal end of the guide tube into the lumen and placed alongside the first stent subsequently to deployment of the first stent off of the distal end of the guide tube.

For some applications, a distal end of the second stent is disposed proximally to the hole.

For some applications the apparatus further includes a guidewire configured to (i) enter a lumen of the guide tube from a distal-end opening of the guide tube, (ii) pass out of the lumen of the guide tube at the guidewire-engaging portion of the guide tube, and (iii) pass into the lumen of the guide tube through the hole, and the first stent is (i) constrained from distal motion past the guidewire-engaging portion when the guidewire is disposed within the guidewire-engaging portion, and (ii) constrained from proximal motion past the hole when the guidewire is disposed within the hole.

For some applications, the first stent is slidably deployable off the distal end of the guide tube when the guidewire is not disposed within the guidewire-engaging portion.

For some applications, there is no hole in the wall of the guide tube that is within 10 mm from the distal end of the guide tube.

For some applications, there is no hole having a diameter of less than 1 cm in the wall of the guide tube that is within 10 mm from the distal end of the guide tube For some applications the apparatus further includes a guidewire that (i) enters a lumen of the guide tube from a distal-end opening of the guide tube, (ii) passes out of the lumen of the guide tube at the guidewire-engaging portion of the guide tube, and (iii) passes into the lumen of the guide tube through the hole, and
  the first stent (a) has an outer surface disposed against the guidewire and (b) is configured to be advanced into the lumen of the subject while the outer surface is disposed against the guidewire, and
  the second stent, surrounds the guidewire, and is configured to be advanced into the lumen of the subject over the guidewire.

For some applications, a distance between the distal end of the guide tube and the hole is 4-18 cm.

For some applications, the guidewire-engaging portion is shaped to define a slit extending proximally along the wall of the guide tube, from the distal end of the guide tube, the slit having a length of 1 mm-7 cm.

For some applications, the slit has a length of 2.5-3 cm.

For some applications, the guidewire-engaging portion is shaped to define a weak spot configured to tear in response to force applied to the weak spot by a guidewire.

There is further provided in accordance with some applications of the present invention, apparatus including:
  a guide tube shaped to define a proximal end and a distal end of the guide tube;
  a first stent surrounding the guide tube so as to be advanceable together with the guide tube into a lumen of a subject, and being slidably deployable off of the distal end of the guide tube;
  a second stent, proximal to the first stent, surrounding a proximal portion of the guide tube, and shaped and sized to be advanceable along the guide tube into the lumen;
  a first lock, which prevents proximal motion of the first stent past a location that is at least 1 mm from a distal end of the second stent; and
  a second lock, which prevents distal motion of the second stent past a location that is at least 1 mm proximal of a proximal end of the first stent.

For some applications, the guide tube is shaped to define two holes in a lateral wall of the guide tube, and the first lock includes a locking wire that passes through the two holes.

For some applications:
  the second stent is shaped to define a hole in a portion of the second stent,
  the apparatus further includes a pushing tube, disposed proximally to the second stent and configured to push the second stent off of the guide tube,
  the pushing tube is shaped to define a hole in a portion of the pushing tube, and
  the second lock includes a locking wire that passes through the hole in the portion of the second stent and through the hole in the portion of the pushing tube.

For some applications, the first lock includes a first locking wire, and the second lock includes a second locking wire.

For some applications, a distance between the proximal end of the first stent and the distal end of the second stent is a fixed distance.

For some applications, a distance between the proximal end of the first stent and the distal end of the second stent is 2-80 mm.

For some applications, the distance between the proximal end of the first stent and the distal end of the second stent is at least 5 mm.

For some applications, the distance between the proximal end of the first stent and the distal end of the second stent is less than 25 mm.

For some applications, the first lock is configured to prevent distal motion of the first stent during advancement of the first stent on the guide tube into the lumen of the subject.

For some applications the apparatus further includes a guidewire,
  the guide tube is further shaped to define (a) a guidewire-engaging portion at a distal portion of the guide tube, a proximal end of the guidewire-engaging portion being located distally to a proximal end of the guide tube, and (b) a hole in a wall of the guide tube, the hole being located proximally to the proximal end of the guidewire-engaging portion and distally to a proximal end of the guide tube,
  the first stent is (i) constrained from distal motion past the guidewire-engaging portion when the guidewire is disposed within the guidewire-engaging portion, and (ii) constrained from proximal motion past the hole when the guidewire is disposed within the hole, and
  the first lock is not arranged to utilize the guidewire to prevent distal motion of the first stent.

There is further provided in accordance with some applications of the present invention, apparatus including:
  a guide tube shaped to define a proximal end and a distal end of the guide tube;
  a first stent surrounding the guide tube so as to be advanceable together with the guide tube into a lumen of a subject, and being slidably deployable off of the distal end of the guide tube;
  a second stent, proximal to the first stent, surrounding a proximal portion of the guide tube, and shaped and sized to be advanceable along the guide tube into the lumen; and
  a lock, which prevents distal motion of the second stent beyond a proximal end of the first stent when the first stent is being slidably deployed off of the distal end of the guide tube, and unlockable subsequently to the deployment of the first stent off of the distal end of the guide tube to allow deployment of the second stent off of the guide tube.

For some applications:
  the second stent is shaped to define a hole in a portion of the second stent, the apparatus further includes a pushing tube, disposed proximally to the second stent and configured to push the second stent off of the guide tube, the pushing tube is shaped to define a hole in a portion of the pushing tube, and the second lock includes a locking wire that passes through the hole in the portion of the second stent and through the hole in the portion of the pushing tube.

There is further provided in accordance with some applications of the present invention, a method including:

using apparatus including:
  a guide tube shaped to define a proximal end and a distal end of the guide tube;
  a first stent surrounding a distal portion of the guide tube, and
  a second stent, proximal to the first stent, surrounding a proximal portion of the guide tube;

advancing the apparatus to a desired location in a lumen of a subject while: (a) the first stent is constrained from proximal motion past a location that is at least 1 mm from a distal end of the second stent, and (b) the second stent is constrained from distal motion beyond a location that is at least 1 mm proximal of a proximal end of the first stent.

For some applications:

subsequently to the advancing of the apparatus, and while the second stent is constrained from distal motion, withdrawing the guide tube with respect to the first stent, until the first stent is deployed off of the distal end of the guide tube into the lumen;

subsequently to deploying the first stent off of the distal end of the guide tube, releasing the second stent such that it is not constrained from distal motion;

subsequently, advancing the second stent along the guide tube in the lumen of the subject and deploying the second stent off of the distal end of the guide tube alongside the first stent.

There is further provided in accordance with some applications of the present invention, apparatus including:

a guide tube shaped to define a guidewire-engaging portion at a distal portion of the guide tube, a proximal end of the guidewire-engaging portion being located distally to a proximal end of the guide tube;
  a first stent surrounding the guide tube so as to be advanceable together with the guide tube into a lumen of a subject, the first stent being slidable along the guide tube such that a distal end of the first stent is disposed proximally to the guidewire-engaging portion of the guide tube;
  a guidewire arranged (i) entering a lumen of the guide tube from a distal-end opening of the guide tube, (ii) disposed in the guidewire-engaging portion, and (iii) passing out of the lumen of the guide tube proximally to the guidewire-engaging portion of the guide tube, such that the first stent is constrained from distal motion past the guidewire-engaging portion by the guidewire being disposed within the guidewire-engaging portion; and
  a second stent, proximal to the first stent, surrounding a proximal portion of the guide tube and the guidewire, and shaped and sized to be advanceable along the guide tube, and:
    (i) the guidewire is positioned to laterally exit the guidewire-engaging portion without being advanced distally or proximally,
    (ii) the first stent is slidably deployable off of the distal end of the guide tube upon the guidewire having exited the guidewire-engaging portion, without the guidewire having been moved proximally subsequent to the guidewire exiting the guidewire-engaging portion, and
    (iii) the second stent is slidably deployable off of the distal end of the guide tube and placeable alongside the first stent subsequently to deployment of the first stent off of the distal end of the guide tube, without the guidewire having been moved proximally subsequent to the guidewire exiting the guidewire-engaging portion.

For some applications, the first stent (a) has an outer surface disposed against the guidewire and (b) is configured to be advanced into the lumen of the subject while the outer surface is disposed against the guidewire.

For some applications, the guidewire-engaging portion is shaped to define a slit extending proximally along a wall of the guide tube, from a distal end of the guide tube, the slit having a length of 1-70 mm.

For some applications, the slit is shaped to define two slit lips that are in contact with each other to define a closed-slit configuration in the absence of any forces applied to the slit lips, and disengageable from each other, by application of a force to the lips, to define an opened-slit configuration.

For some applications, the slit is shaped to define two slit lips that are in contact with each other to define a closed-slit configuration, and disengageable from each other to define an opened-slit configuration, and further including a lock which:
  presses the slit lips against each other in the closed-slit configuration when the guidewire is disposed in the guidewire-engaging portion to inhibit the lateral exiting of the guidewire from the guidewire-engaging portion, and
  allows the lateral exiting of the guidewire from the guidewire-engaging portion in the opened-slit configuration when the lock does not press the slit lips against each other.

For some applications, the guidewire-engaging portion is shaped to define a weak spot configured to (i) tear in response to force applied to the weak spot by the guidewire upon the distal portion of the guide tube being withdrawn into the first stent, and (ii) shaped and sized to allow passage of the guidewire therethrough in the teared state thereof.

For some applications, the apparatus further includes:
  a first lock, which prevents proximal motion of the first stent past a location that is at least 1 mm from a distal end of the second stent; and
  a second lock, which prevents distal motion of the second stent past a location that is at least 1 mm proximal of a proximal end of the first stent.

For some applications, the guide tube is shaped to define two holes in a lateral wall of the guide tube, and wherein the first lock includes a locking wire that passes through the two holes.

For some applications:
  the second stent is shaped to define a hole in a portion of the second stent,
  the apparatus further includes a pushing tube, disposed proximally to the second stent and configured to push the second stent off of the guide tube,
  the pushing tube is shaped to define a hole in a portion of the pushing tube, and
  the second lock includes a locking wire that passes through the hole in the portion of the second stent and through the hole in the portion of the pushing tube.

For some applications, the first lock includes a first locking wire, and wherein the second lock includes a second locking wire.

For some applications, the first lock is configured to prevent distal motion of the first stent during advancement of the first stent on the guide tube into the lumen of the subject.

The present invention will be more fully understood from the following detailed description of applications thereof, taken together with the drawings, in which:

DETAILED DESCRIPTION OF EMBODIMENTS

A guide tube is provided for facilitating deployment of more than one stent (e.g., a first and a second stent) in a lumen of the subject. In accordance with some applications of the present invention, various configurations of the guide tube are descried herein. Specifically, FIGS. 1-4 illustrate guide tube 22, and FIGS. 5-9D illustrate guide tube 220, in accordance with some applications of the present invention. It is noted that both guide tube 22 and guide tube 220 are configured to deliver the first and second stents into the lumen of the subject without removing guide tubes 22 and 220 or a guidewire used during the procedure from the body of the subject following deployment of the first stent and prior to mounting the second stent. The first and second stents are typically mounted onto guide tubes 22 and 220 in advance of a procedure, and subsequently advanced into the subject's body to be deployed within the lumen of the subject, as will be described hereinbelow.

The present detailed description begins with a description of a guide tube 22, which is used to deploy multiple stents in a lumen of the subject, in accordance with some applications of the present invention.

Figure 1:
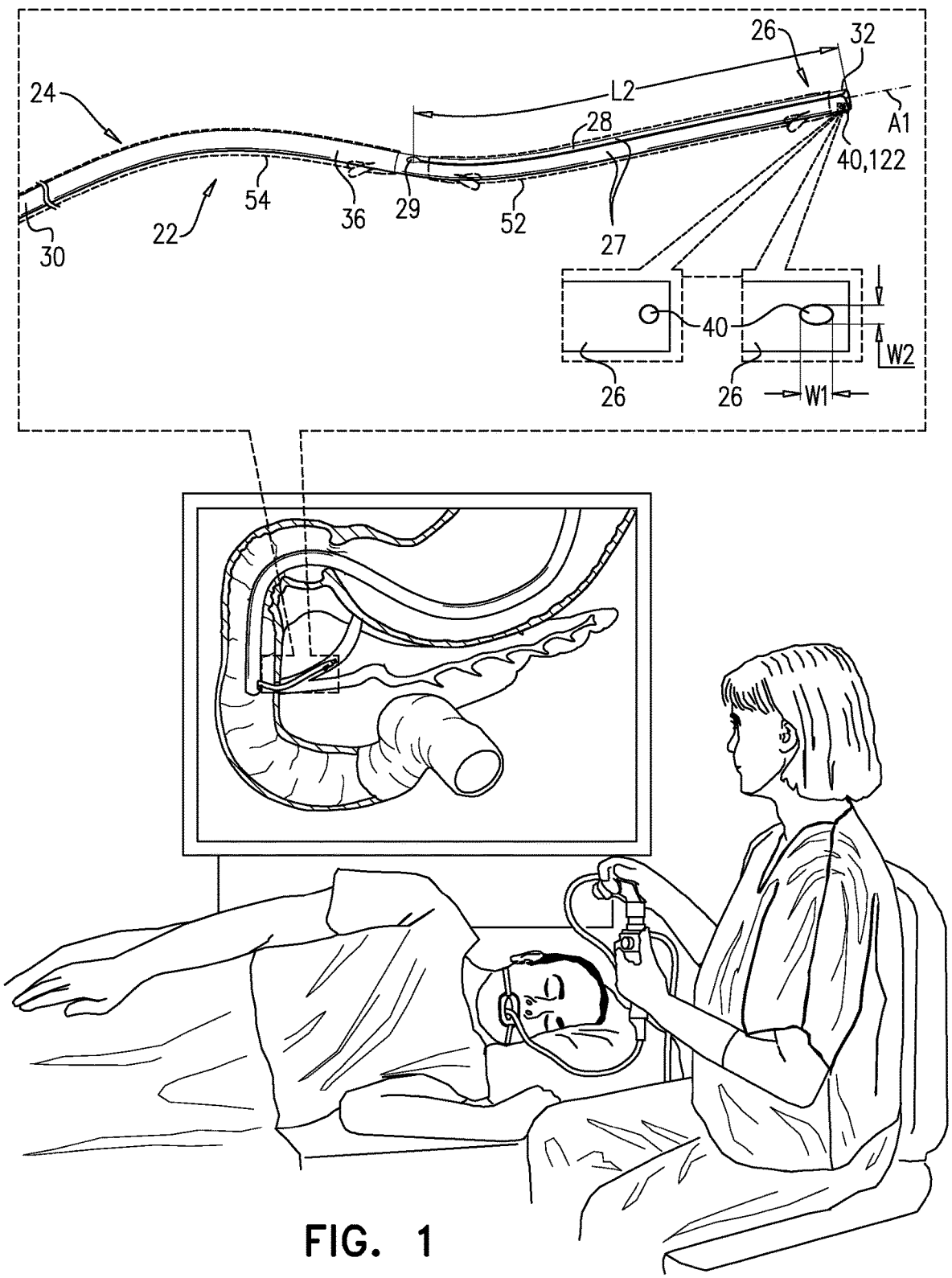
FIG. 1 is a schematic illustration of a guide tube for deployment of a first and second stent in a lumen of a subject, in accordance with some applications of the present invention.
Figure 2:
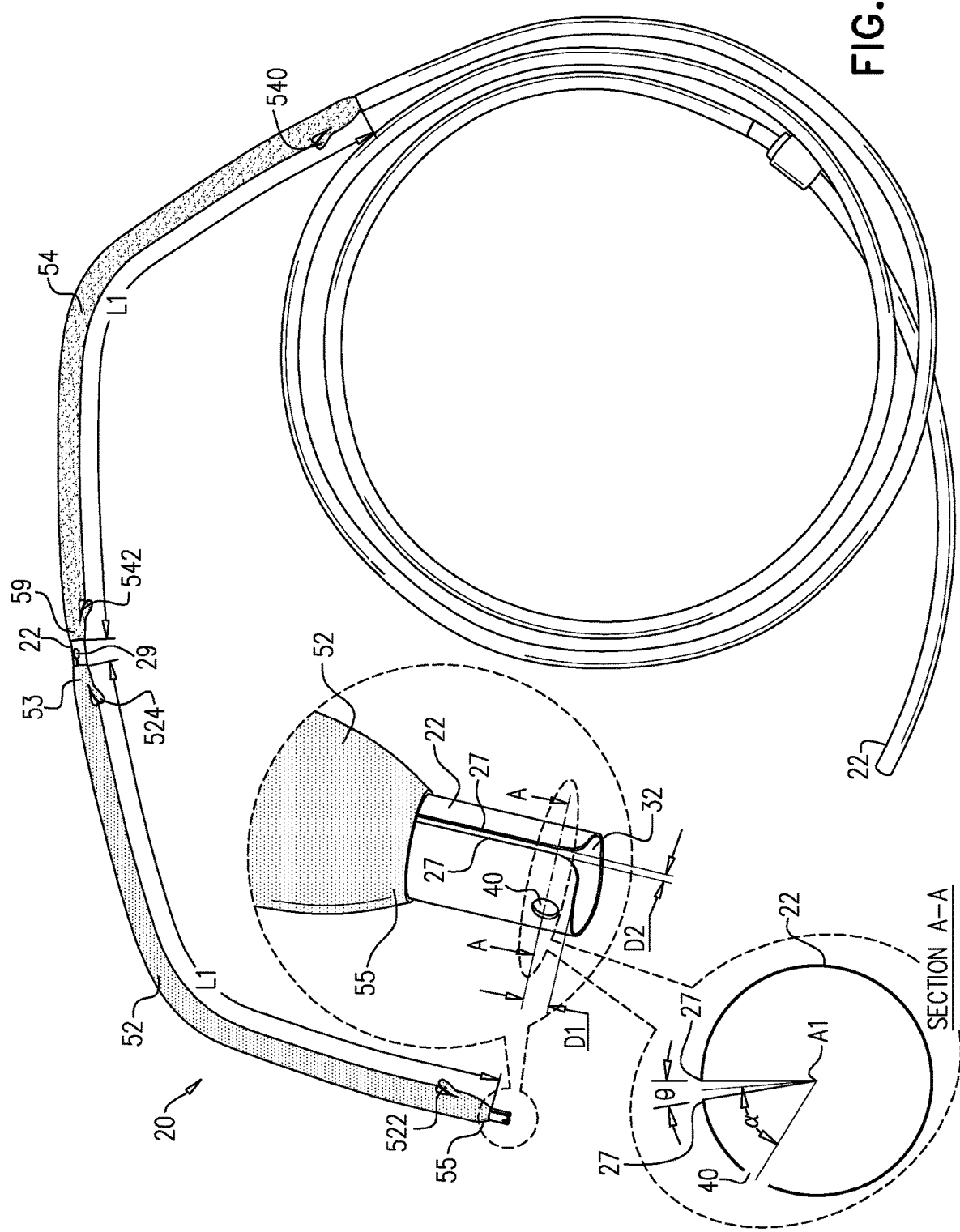
FIG. 2 is a schematic illustration of apparatus for delivery and deployment of a first and second stent in a lumen of a subject, in accordance with some applications of the present invention.

Reference is made to FIGS. 1 and 2.

FIG. 1 is a schematic illustration of guide tube 22, in accordance with some applications of the present invention. As shown, guide tube 22 is shaped to define a proximal end 30 at a proximal portion 24 of guide tube 22, and a distal end 32 at a distal portion 26 of guide tube 22.

Guide tube 22 is additionally shaped to define a guidewire-engaging portion 122, shown as a hole 40 through a wall 36 of guide tube 22 at distal portion 26 of the guide tube. Guide tube 22 is further additionally shaped to define a slit 28 extending proximally along wall 36 of guide tube 22, from distal end 32 of the guide tube. A proximal end 29 of slit 28 is located distally to proximal end 30 of guide tube 22. Additionally, proximal end 29 of slit 28 is located proximally to hole 40.

Typically, hole 40 is disposed at an angular offset alpha of 90-180 degrees, e.g., 180 degrees, from slit 28, with respect to a central longitudinal axis A1 of the guide tube. Alternatively, a smaller angle alpha is used (e.g., an angle alpha of approximately 60 degrees is shown in FIG. 2). As used in the present application, including in the claims, a "central longitudinal axis" of an elongate structure is the set of all centroids of transverse cross-sectional sections of the structure along the structure. Thus, the cross-sectional sections are locally perpendicular to the central longitudinal axis, which runs along the structure. (If the structure is circular in cross-section, the centroids correspond with the centers of the circular cross-sectional sections.) The central longitudinal axis of a curved elongate structure is curved, rather than straight.

Typically, a distance D1 between a center of hole 40 and distal end 32 of guide tube 22 is at least 5 mm and/or less than 200 mm e.g., between 5 and 200 mm.

For some applications, hole 40 is shaped to define an elliptical hole having a major axis W1 which is typically oriented in parallel with longitudinal axis A1 of guide tube 22. The major axis is typically 1.5-4 times longer than a minor axis W2 of hole 40. For example, hole 40 has major axis W1 having a length of 5-10 mm and minor axis W2 having a length of 0.5-1.0 mm.

Slit 28 defines two slit edges 27 that are parallel to central longitudinal axis A1 of guide tube 22, typically a distance D2 between a first one of the slit edges and a second one of the slit edges being 0.45-0.9 mm. For some applications, when guide tube 22 is viewed from distal end 32 of guide tube 22, an angle theta of 10-80 degrees, e.g., 20-70 degrees, is formed that is defined by: (a) a first line extending from the central longitudinal axis to a first one of the slit edges, and (b) a second line extending from the central longitudinal axis to a second one of the slit edges.

Reference is still made to FIGS. 1 and 2. FIG. 2 is a schematic illustration of apparatus 20 for delivery and deployment of a first stent 52 and a second stent 54 in a lumen of a subject, in accordance with some applications of the present invention.

For some applications, apparatus 20 comprises guide tube 22 (as described hereinabove with reference to FIG. 1), and first and second stents 52 and 54 respectively. As shown, first and second stents 52 and 54 surround guide tube 22, second stent 54 being disposed proximally to first stent 52 and surrounding proximal portion 24 of guide tube 22. First stent 52 is typically disposed over guide tube 22 such that a proximal end 53 of first stent 52 is disposed distally to proximal end 29 of slit 28 of guide tube 22 while a distal end 55 of first stent 52 is disposed proximally to hole 40.

First stent 52 is shaped to define a proximal flap 524 and a distal flap 522, and second stent 54 is shaped to define a proximal flap 540 and a distal flap 542. The flaps are generally configured to facilitate anchoring of the stents to lumens in which the stents are deployed.

For some applications, a distal end 59 of second stent 54 is disposed proximally to proximal end 29 of slit 28. For other applications, distal end 59 of second stent 54 is disposed distally to proximal end 29 of slit 28.

First stent 52 is slidably deployed off of distal end 32 of guide tube 22. Additionally, second stent 54, is also shaped and sized to be advanceable over guide tube 22, typically subsequently to deployment of first stent 52 off of distal end 32 of guide tube 22.

For some applications, first and second stents 52 and 54 each have a length L1 of 5-15 cm, and slit 28 also has a length L2 of 5-15 cm. Typically, slit 28 has a length that is greater than the length of first stent 52. For some applications, slit 28 has a length that is: (a) greater than a length of first stent 52, and (b) less than a sum of the length of first stent 52 and a length of second stent 54.

Apparatus 20 is typically advanced into a lumen of the subject, and guide tube 22 facilitates placement of first and second stents 52 and 54 within the lumen of the subject.

Reference is now made to FIGS. 3A-H, which depict a general overview of a method for use of apparatus 20 for deploying first and second stents 52 and 54 in a lumen of a subject, in accordance with some applications of the present invention. Typically, stents 52 and 54 are deployed in the lumen of the subject, e.g., a common bile duct of the subject, in order to manage strictures of the lumen. In accordance with some applications of the present invention, apparatus 20 is configured such that first stent 52 is advanced into the lumen of the subject against a guidewire, and second stent 54 is advanced into the lumen over the guidewire (i.e., surrounding the guidewire).

Figure 3A:
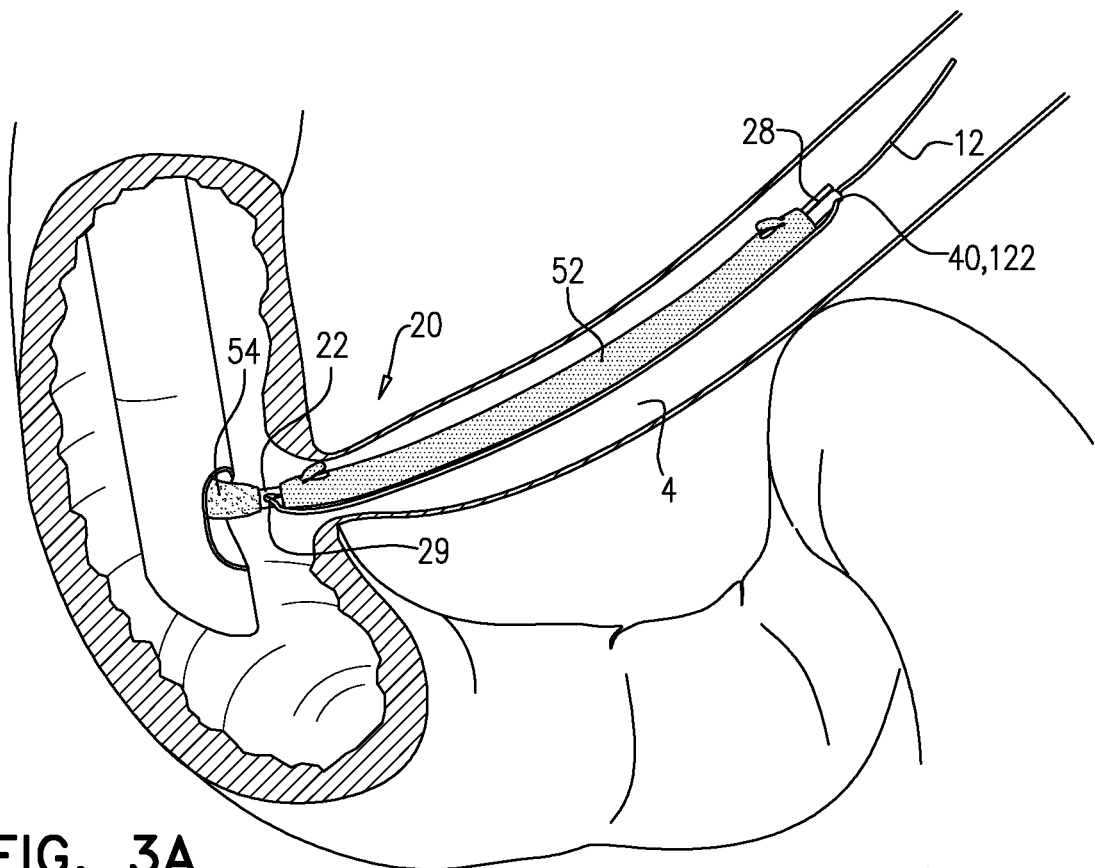
FIGS. 3A-H are schematic illustrations depicting a general overview of a method for deploying first and second stents in a lumen of a subject, in accordance with some applications of the present invention.

Reference is made to FIG. 3A. In accordance with some applications of the present invention, apparatus 20 (comprising guide tube 22 and first and second stents 52 and 54, as described hereinabove with reference to FIG. 2) is used in combination with a guidewire 12 to deploy stents 52 and 54 alongside each other in the lumen. Guidewire 12 is typically threaded through guide tube 22 such that following the threading:

(a) guidewire 12 enters a lumen of guide tube 22 from a distal-end 32 opening of guide tube 22,
(b) guidewire 12 passes out of the lumen of guide tube 22 through hole 40 of guide tube 22,
(c) first stent 52 is constrained from distal motion past hole 40 of guide tube 22, due to guidewire 12 being disposed within hole 40,
(d) guidewire 12 passes into the lumen of guide tube 22 through proximal end 29 of slit 28, and
(e) first stent 52 is constrained from proximal motion past proximal end 29 of slit 28, due to guidewire 12 being disposed within slit 28.

Following threading of guidewire 12 through guide tube 22 as described hereinabove, apparatus 20 is advanced into a body of the subject, e.g., into the small intestine, and into lumen 4 of the common bile duct, as shown in FIG. 3A. As shown, first stent 52 is advanced distally over guide tube 22 and against guidewire 12 (i.e., an outer surface of first stent 52 is disposed against guidewire 12). Due to threading of guidewire 12 as described hereinabove, stent 52 is advanced distally in lumen 4 while it is constrained from distal motion past hole 40 of guide tube 22. Constrained motion of stent 52 (particularly due to guidewire 12 being disposed within hole 40) typically allows for stent 52 to be advanced to a desired deployment site within lumen 4 in a controlled manner (i.e., inhibiting uncontrolled distal motion of stent 52, thus allowing the physician to safely perform the implantation at the desired deployment site).

Additionally, due to guidewire 12 being disposed within slit 28, first stent 52 is constrained from proximal motion past proximal end 29 of slit 28, allowing the physician to advance stent 52 in a controlled manner.

Reference is now made to FIGS. 3B-H.

Figure 3B:
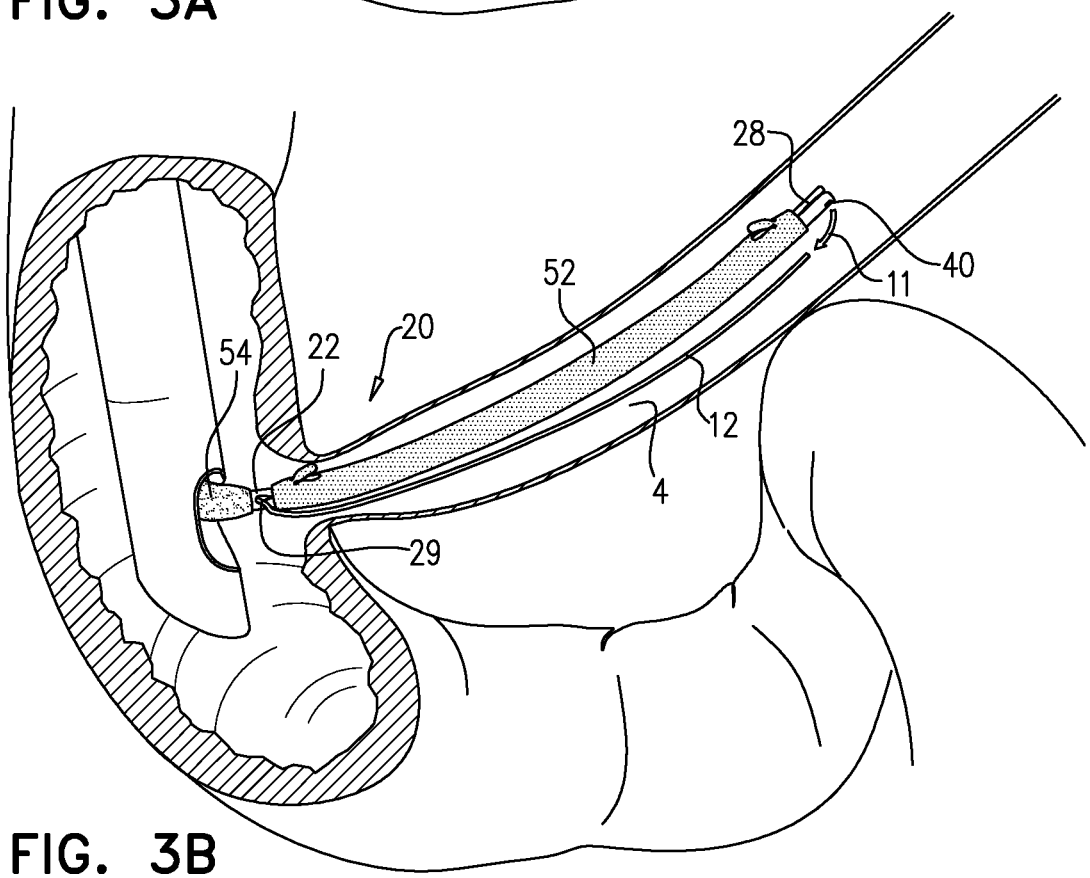
Figure 3C:
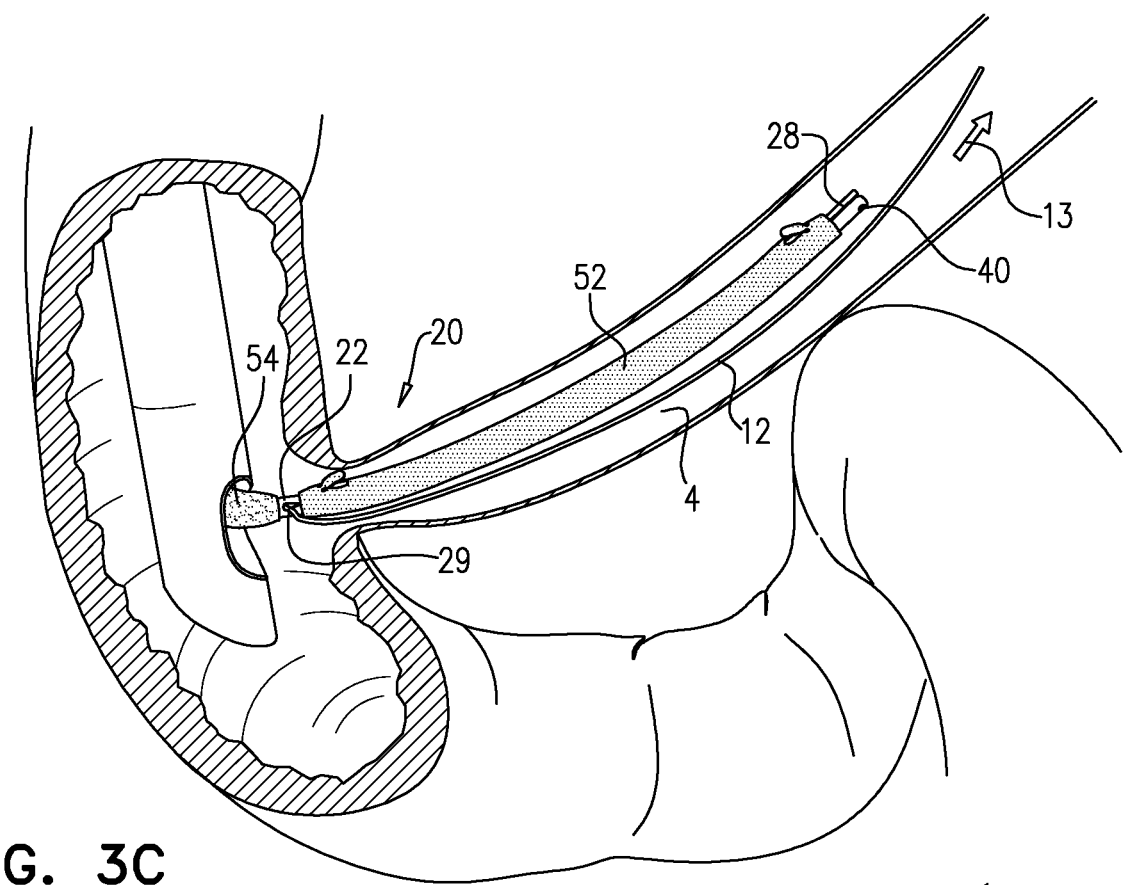
Figure 3D:
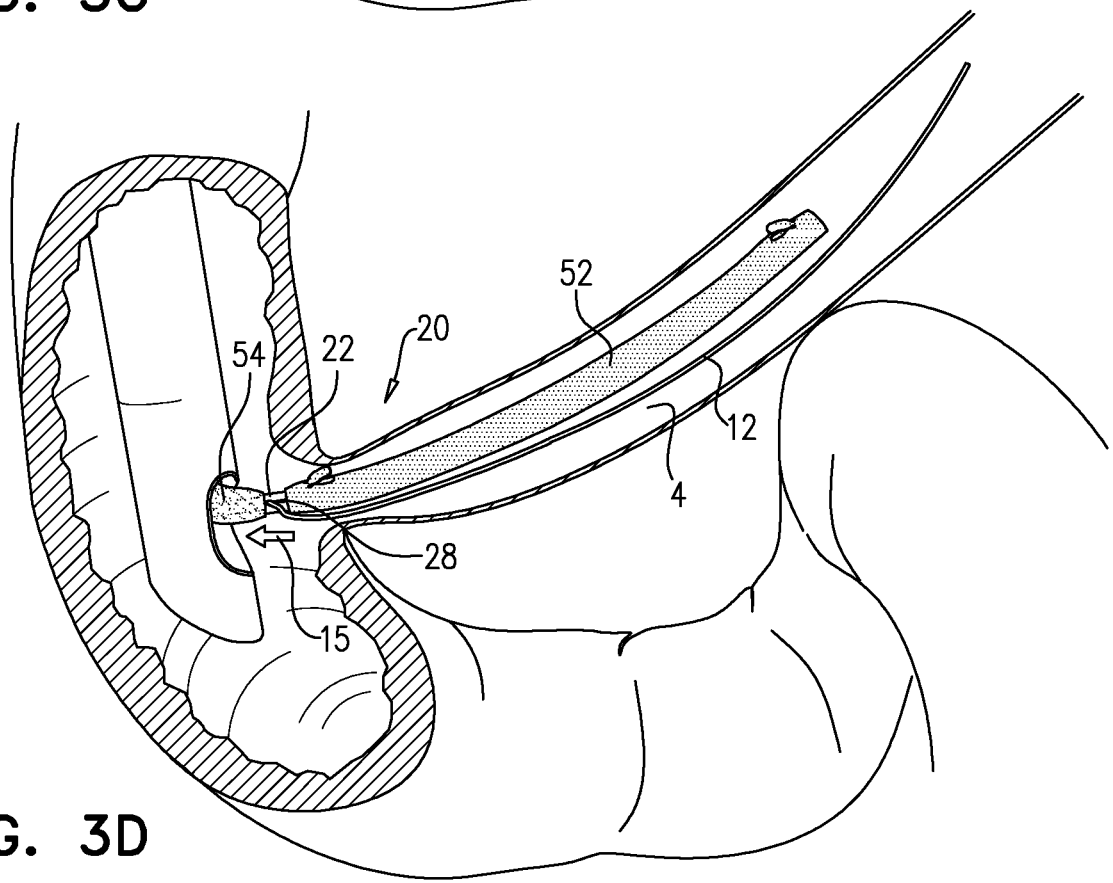
Figure 3E:
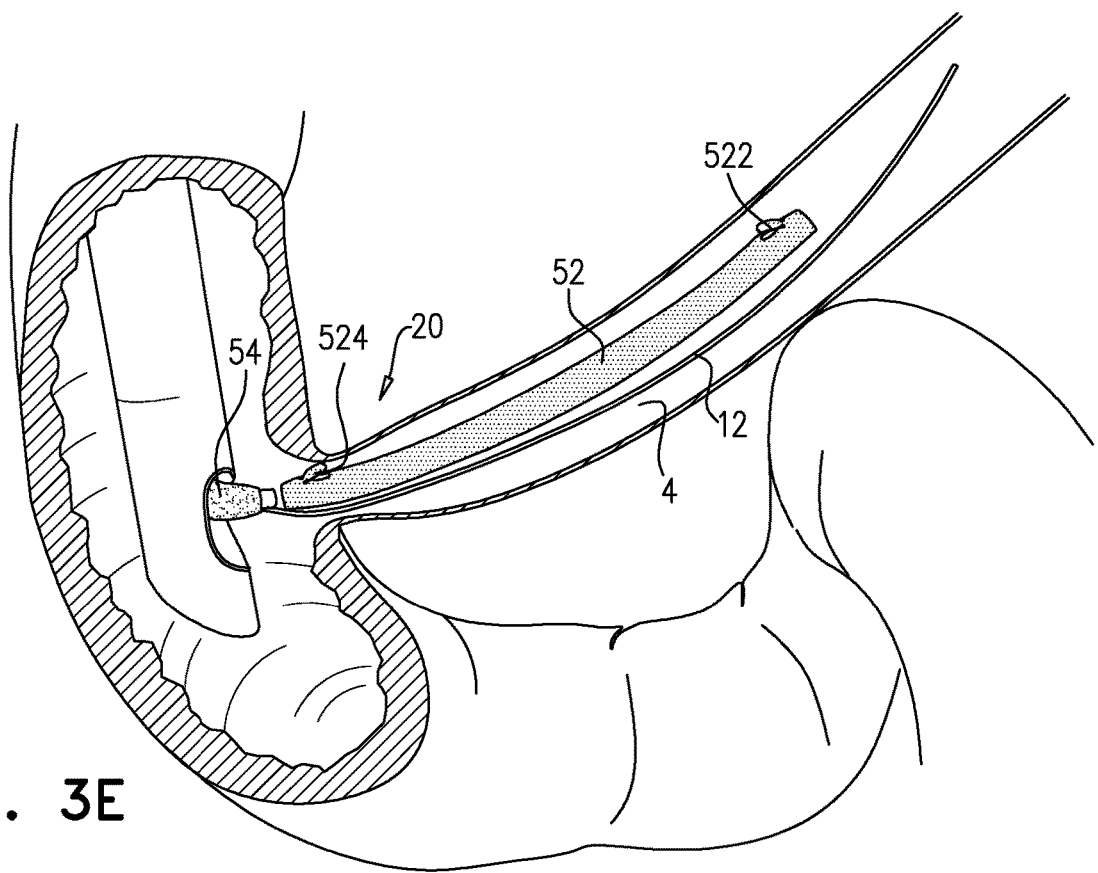

When first stent 52 reaches a desired deployment site within lumen 4, guidewire 12 is removed from hole 40 of guide tube 22, by pulling guidewire 12 proximally in the direction indicated by arrow 11, as shown in FIG. 3B. Guidewire 12 is then typically advanced distally in lumen 4 as indicated by arrow 13 (FIG. 3C). Guidewire 12 is thus maintained within lumen 4 and is not removed from lumen 4 at this stage. Removal of guidewire 12 from hole 40 typically releases first stent 52 and allows for guide tube 22 to be pulled proximally in the direction indicated by arrow 15 until guide tube 22 is removed from stent 52, and stent 52 can be deployed in lumen 4 (FIG. 3D). While pulling guide tube 22 proximally in the direction indicated by arrow 15, guidewire 12 slides through slit 28 of guide tube 22 and is consequently centered within a lumen of the guide tube (FIG. 3E). Centering of guidewire 12 in guide tube 22 facilitates using guidewire 12 for deployment of second stent 54 within lumen 4. Positioning of guidewire 12 in guide tube 22 using slit 28 allows second stent 54 to be advanced over guidewire 12, whereas first stent 52 was advanced against (but not while around) guidewire 12.

Figure 3F:
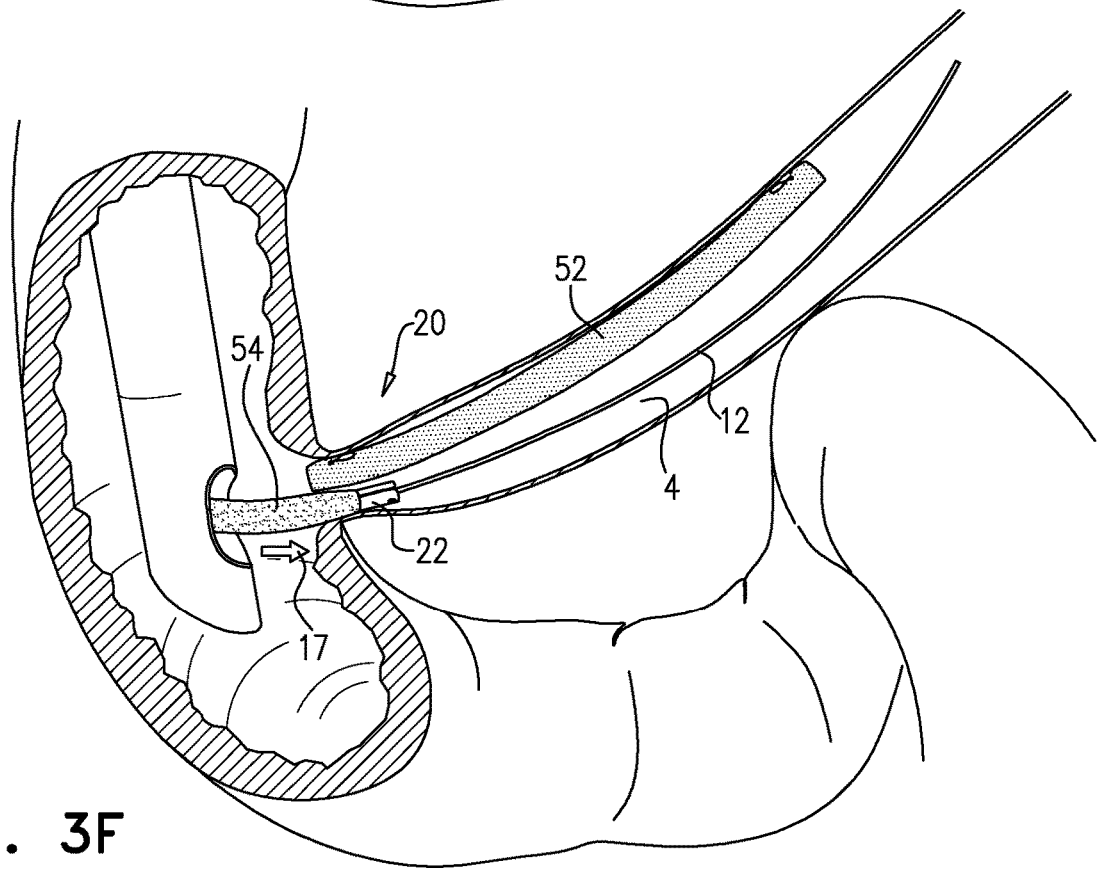
Figure 3G:
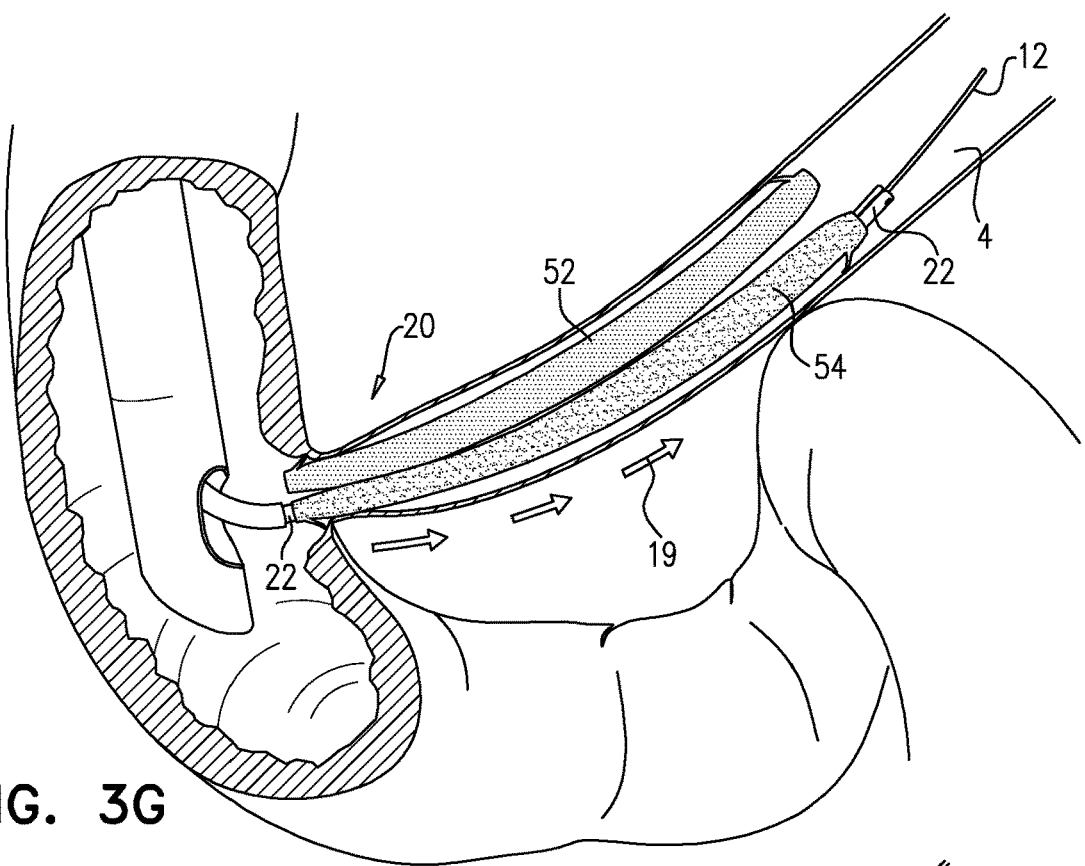
Figure 3H:
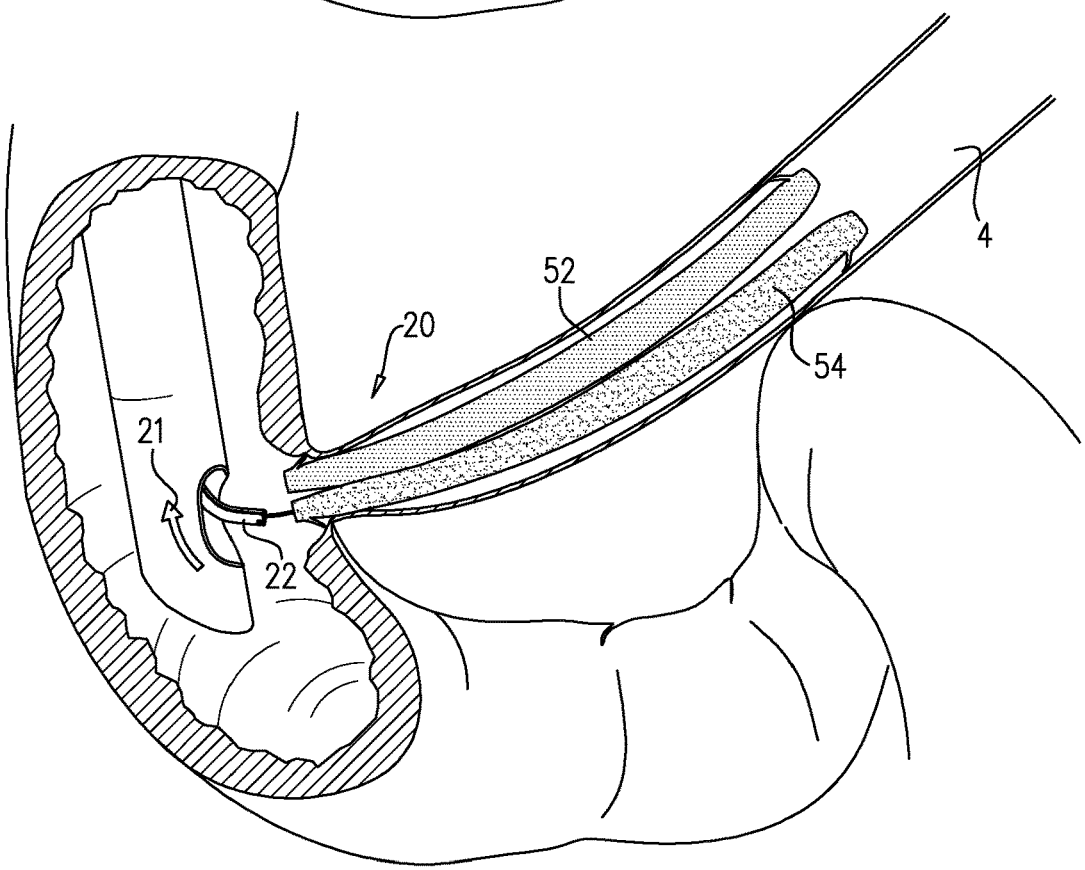

As shown in FIG. 3F, and indicted by arrow 17, second stent 54 is advanced distally in lumen 4 over guide tube 22 and over guidewire 12 (which is the lumen of guide tube 22). As shown in FIG. 3G, second stent 54 continues to be distally advanced in lumen 4 (as indicted by arrows 19) until a desired deployment site is reached alongside first stent 52 (FIGS. 3F-G). Once second stent 54 is deployed alongside first stent 52, guide tube 22 and guidewire 12 are retracted by being pulled in a proximal direction, as indicated by arrow 21 in FIG. 3H.

As described in FIGS. 3A-H, use of apparatus 20 in accordance with some applications of the present invention, allows for deployment of second stent 54 subsequently to deployment of first stent 52, while maintaining guidewire 12 within lumen 4. Additionally, apparatus 20 allows for deployment of second stent 54 subsequently to deployment of first stent 52, without removing apparatus 20 from the body of the subject following deployment of first stent 52 in order to mount second stent 54. Notably, first and second stents 52 and 54 are typically disposed at the same time on guide tube 22 (also as shown in FIG. 2) when advanced into the subject's body, to be deployed within the lumen using the techniques described herein.

Reference is made to FIGS. 1-9D. It is noted that for some applications first and second stents 52 and 54 comprise self-expandable stents.

It is additionally noted that stents are described by way of illustration and not limitation. The scope of the present invention includes the use of any other drainage tube or tube-like structure configured to relieve stricture of a lumen of a subject.

Figure 4:
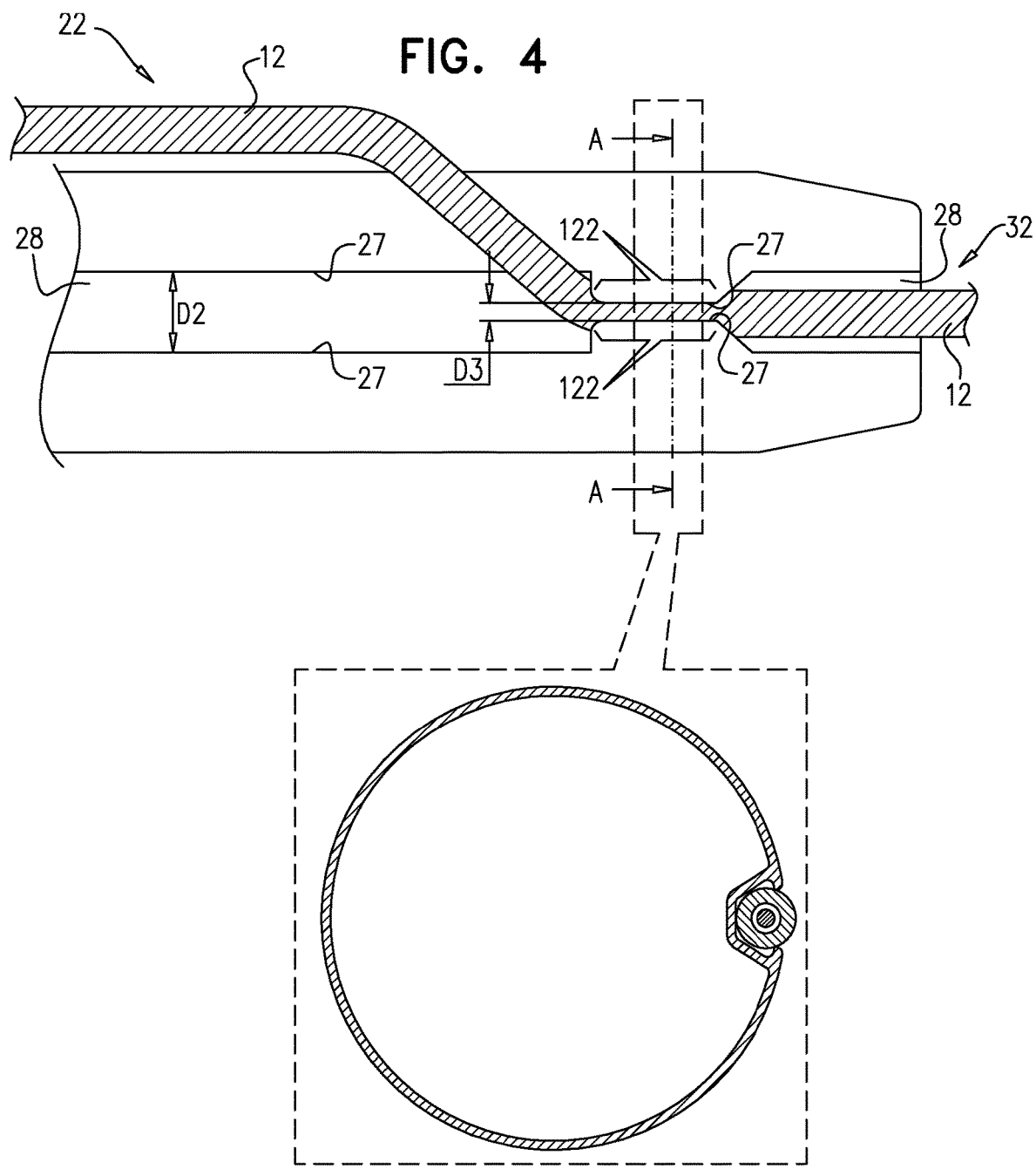
FIG. 4 is a schematic illustration of an additional configuration of the guide tube for deployment of the first and second stents in the lumen of the subject, in accordance with some applications of the present invention.

Reference is now made to FIGS. 3A-4. FIG. 4 is a schematic illustration of an additional configuration of guide tube 22 for deployment of first and second stents 52 and 54 in the lumen of the subject, in accordance with some applications of the present invention. As described hereinabove with reference to FIGS. 1-3H, guidewire-engaging portion 122, embodied as hole 40, is configured to engage guidewire 12 in such a way that it inhibits distal motion of first stent 52 past guidewire-engaging portion 122 of guide tube 22, due to guidewire 12 being engaged by portion 122 (e.g., disposed within hole 40). Guidewire-engaging portion 122 is shown in FIGS. 1-3H as hole 40 by way of illustration and not limitation. It is noted that guidewire-engaging portion 122 may be shaped to define any other configuration suitable for engaging guidewire 12 in such a manner that will grasp or otherwise hold guidewire 12 and thereby inhibit distal motion of first stent 52 past guidewire-engaging portion 122 when stent 52 is advanced distally against guidewire 12. It is noted that the techniques described herein with reference to FIGS. 3A-H apply to guidewire-engaging portion 122 as shown in FIG. 4 as well.

As shown in FIG. 4, for some applications, edges 27 of slit 28 are shaped to define guidewire-engaging portion 122. Typically, distance D2 between a first one of the slit edges and a second one of the slit edges is 0.45-0.9 mm. However, at guidewire-engaging portion 122, a distance D3 between slit edges 27 is smaller than distance D2, such that, for example, D2 is 2-5 times larger than D3. Typically, distance D3 between slit edges 27 is 0.09 mm-0.45 mm, e.g., greater than 0.15 mm and/or less than 0.4 mm. Typically, guidewire-engaging portion 122 shown in FIG. 4 has a length that is 5-10 times longer than D3, e.g., 0.45 mm-4.5 mm, e.g., greater than 1 mm and/or less than 3.5 mm. As shown in FIG. 4, guidewire 12 is typically engaged by, and locked into, the narrowed area in slit 28 which defines guidewire-engaging portion 122. Engaging guidewire 12 by guidewire-engaging portion 122 typically allows for first stent 52 to be advanced to a desired deployment site within the lumen of the subject in a controlled manner (i.e., inhibiting uncontrolled distal motion of stent 52 when stent 52 is advanced distally against guidewire 12, thus allowing the physician to safely perform the implantation at the desired deployment site).

In other words, when guidewire 12 is disposed (i) at least in part in a lumen of guide tube 22, (ii) passing through an opening at distal end 32 of guide tube 22, (iii) passing through guidewire-engaging portion 122 of guide tube 22, and (iv) passing through proximal end 29 of slit 28, first stent 52 is (i) constrained from distal motion past guidewire-engaging portion 122, and (ii) constrained from proximal motion past proximal end 29 of the slit 28. Additionally, when guidewire 12 is disposed (i) at least in part in a lumen of guide tube 22, (ii) passing through an opening at distal end 32 of guide tube 22, (iii) passing through guidewire-engaging portion 122 of guide tube 22, and (iv) passing through proximal end 29 of slit 28, second stent 54 is constrained from distal motion past the proximal end of the slit.

Once first stent 52 is in a desired deployment site in the lumen of the subject, guidewire 12 is released from guidewire-engaging portion 122 by pulling guidewire 12. Removal of guidewire 12 from guidewire-engaging portion 122 typically releases first stent 52 and allows guide tube 22 to be pulled proximally in the direction indicated by arrow 15 (as shown in FIG. 3D) until guide tube 22 is removed from stent 52, and stent 52 can be deployed in the lumen of the subject.

It is noted that for other applications, guidewire-engaging portion 122 may comprise a clip or any other suitable apparatus for engagement of guidewire 12.

Reference is now made to FIGS. 5A-B and 6A-B.

FIGS. 5A-B and 6A-B are schematic illustration of guide tube 220, in accordance with some applications of the present invention. Guide tube 220 is generally the same as guide tube 22 expect for where indicated otherwise.

As shown, guide tube 220 has a distal portion 260 and, proximal thereto, a proximal portion 240. Guide tube 220 is additionally shaped to define a guidewire-engaging portion 222 at distal portion 260 of guide tube 220. Typically, a proximal end 262 of guidewire-engaging portion 222 is located distally to a proximal end 300 of guide tube 220.

Typically, guide tube 220 is additionally shaped to define a hole 400 in the wall of the guide tube 220, hole 400 being located proximally to proximal end 262 of guidewire-engaging portion 222 and distally to proximal end 300 of the guide tube. Typically, a distance between distal end 320 of guide tube 220 and hole 400 is at least 4 cm and/or less than 18 cm (e.g., 4-18 cm). Typically, there is no hole in the wall of guide tube 220 that is within 10 mm from distal end 320 of the guide tube. (More generally, there is typically no hole having a diameter of less than 1 cm in the wall of guide tube 220 that is within 10 mm from distal end 320 of the guide tube.)

For some applications, guidewire-engaging portion 222 is shaped to define a slit 280 extending proximally along the wall of guide tube 220, from distal end 320 of the guide tube. Slit 280 typically has a length of at least 1 mm and/or less than 70 mm (e.g., 1-70 mm). For example, the slit may have a length of at least 25 mm and/or less than 30 mm (e.g., 25-30 mm). A proximal end 262 of slit 280 is located distally to proximal end 300 of guide tube 220. Additionally, proximal end 262 of slit 280 is located distally to hole 400. Typically, proximal end 262 of slit 280 is located 5-40 mm from distal end 320 of the guide tube.

For some applications, slit 280 is shaped to define two lips 282 (hereinafter, "slit lips 282") that are in contact with each other to define a closed-slit configuration in the absence of any forces applied to slit lips 282, and that are disengageable from each other, typically by application of a force to slit lips 282, to define an opened-slit configuration.

Figure 5A:
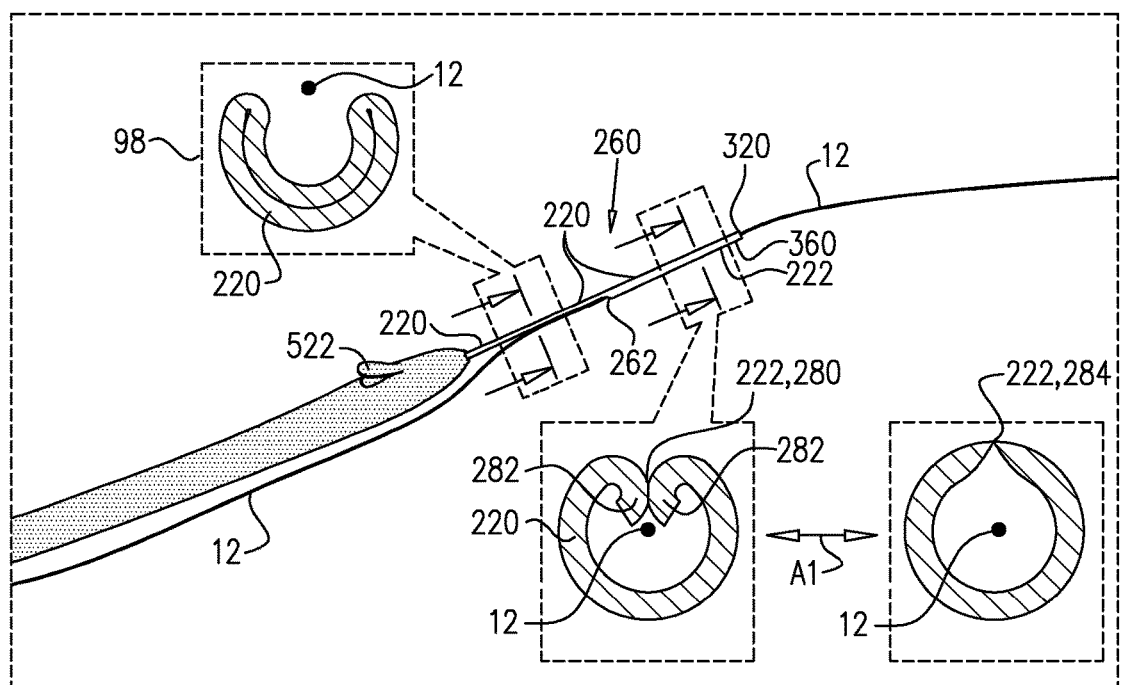
FIGS. 5A-B are schematic illustrations of additional configurations of a distal portion of a guide tube, in accordance with some applications of the present invention.
Figure 5A:
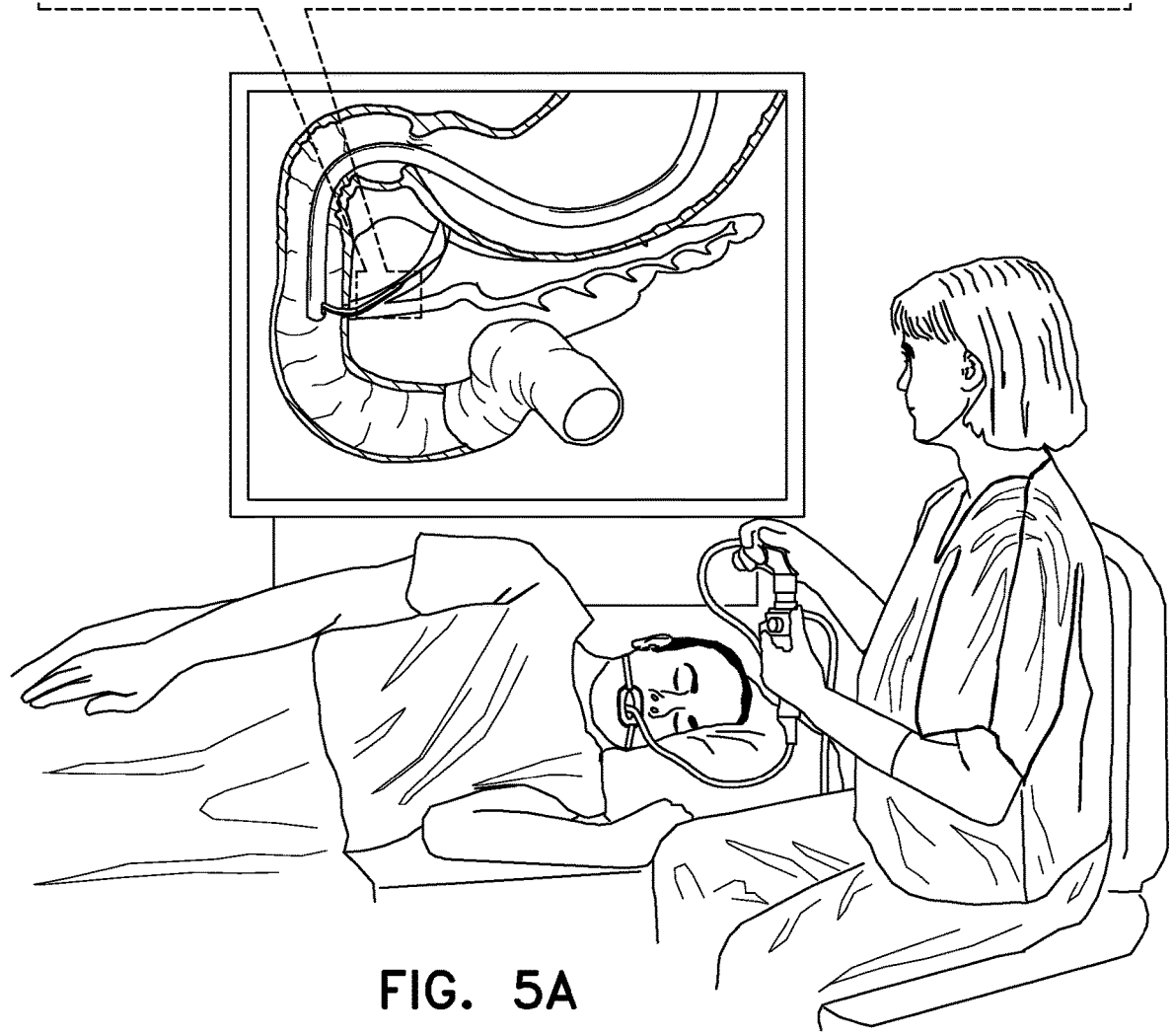
Figure 5B:
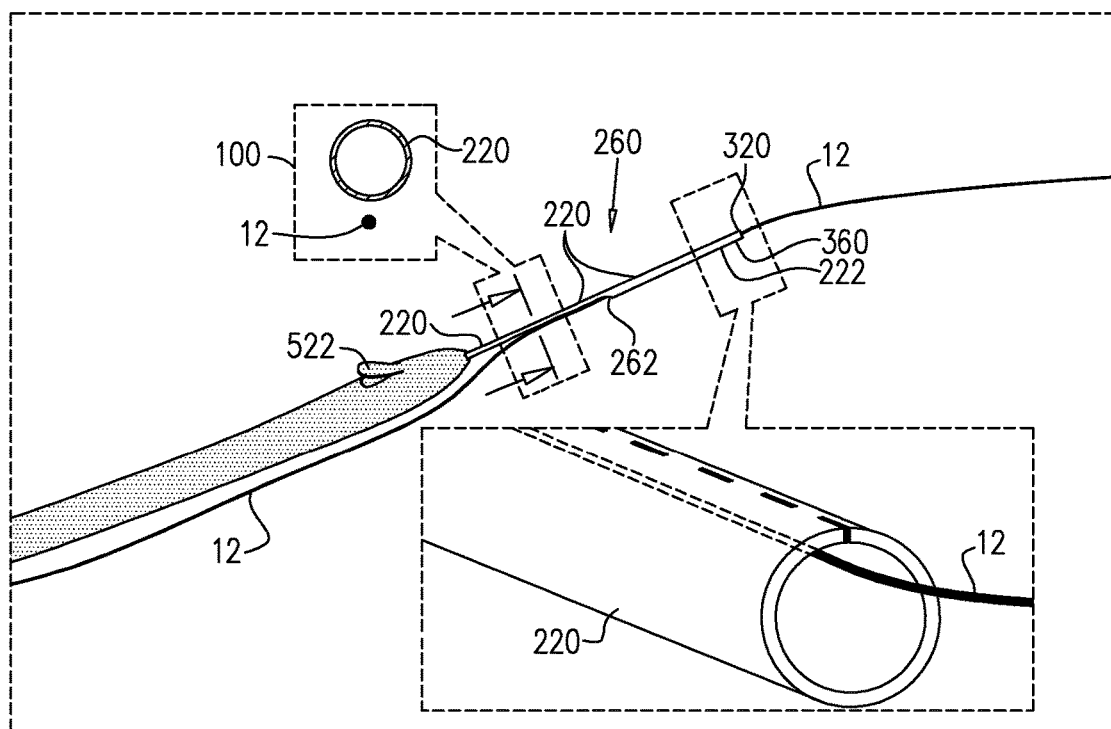
Figure 5B:
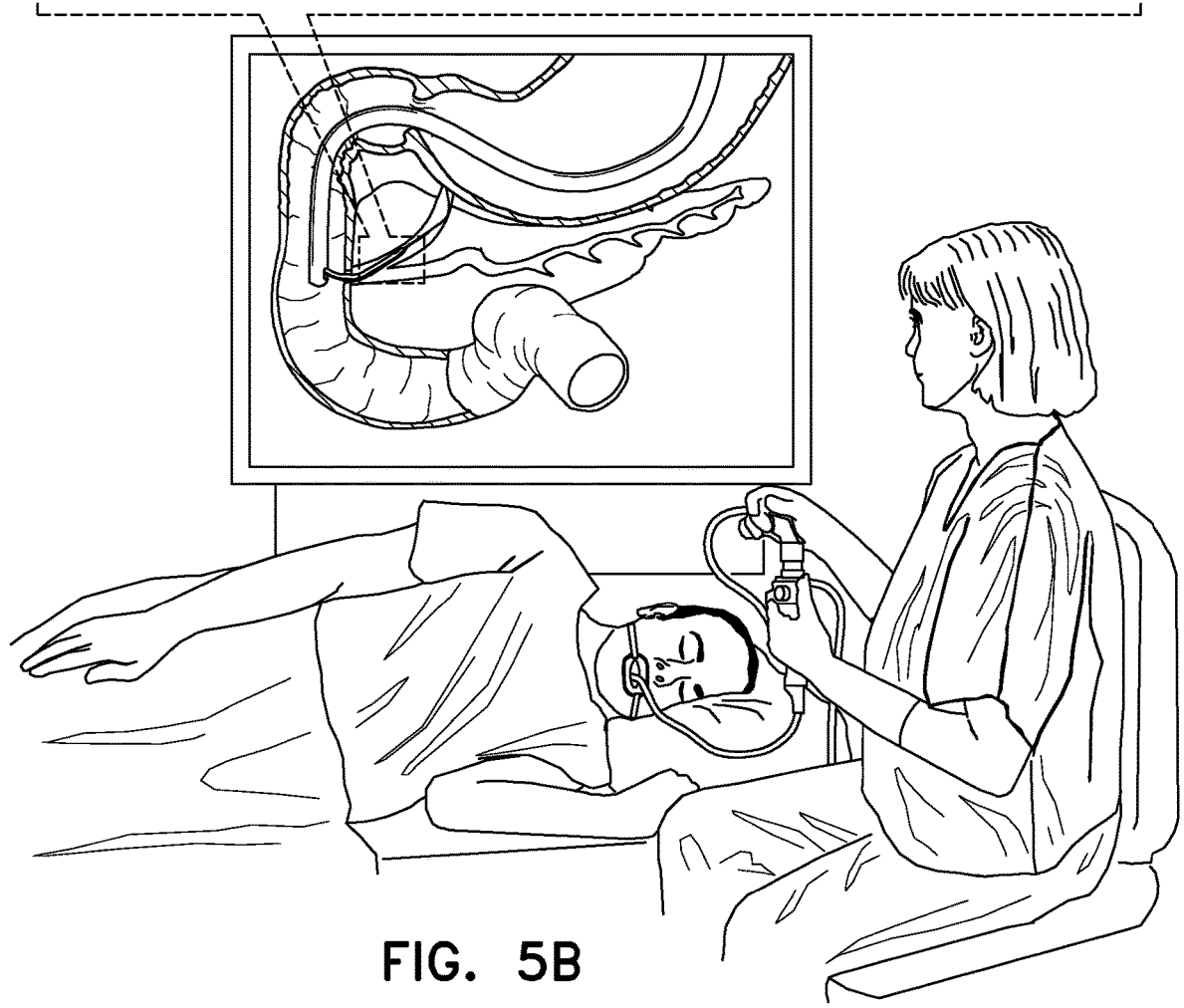
Figure 6A:
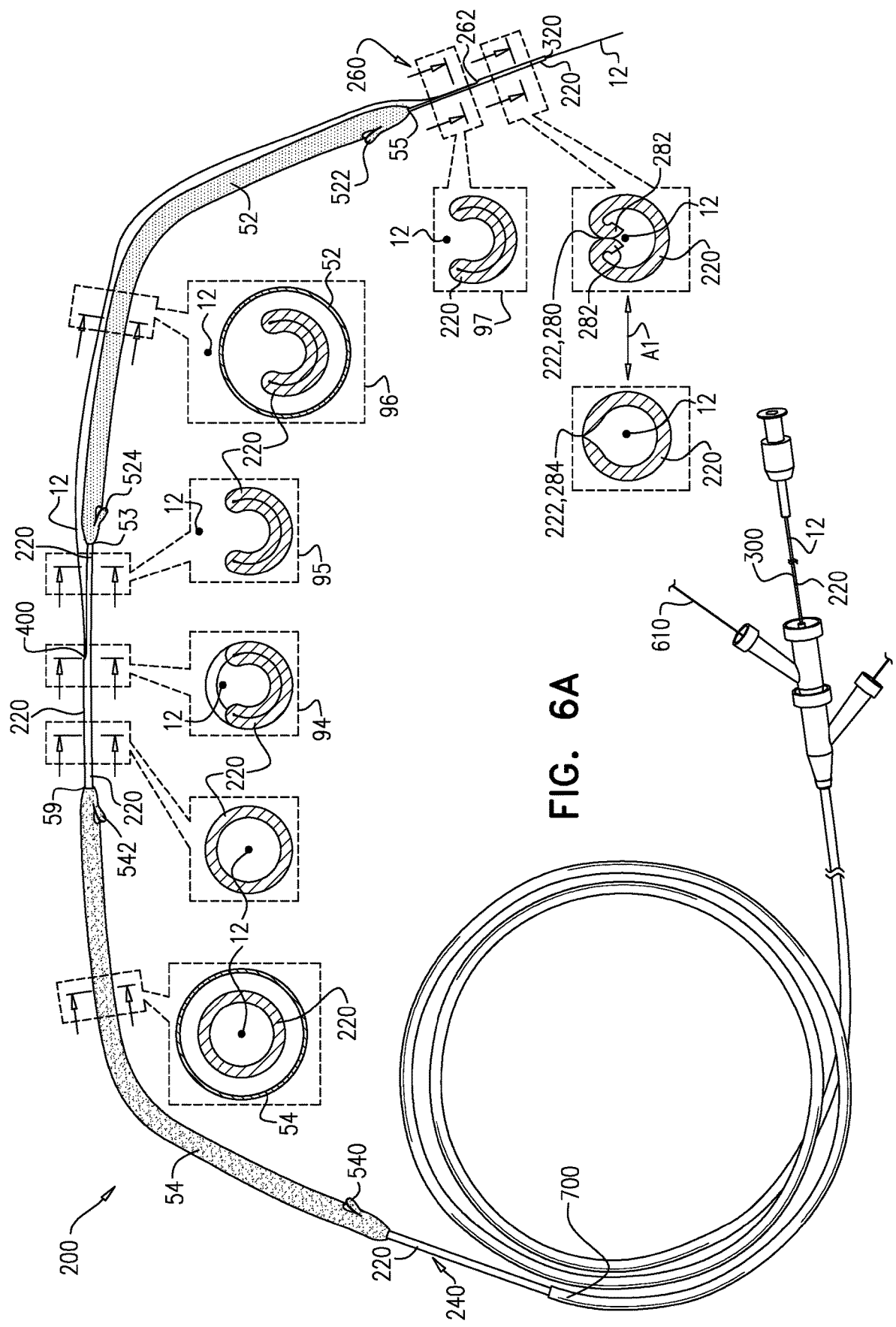
FIGS. 6A-B are schematic illustrations of apparatus for delivery and deployment of a first and a second stent in a lumen of a subject, in accordance with some applications of the present invention.
Figure 6B:
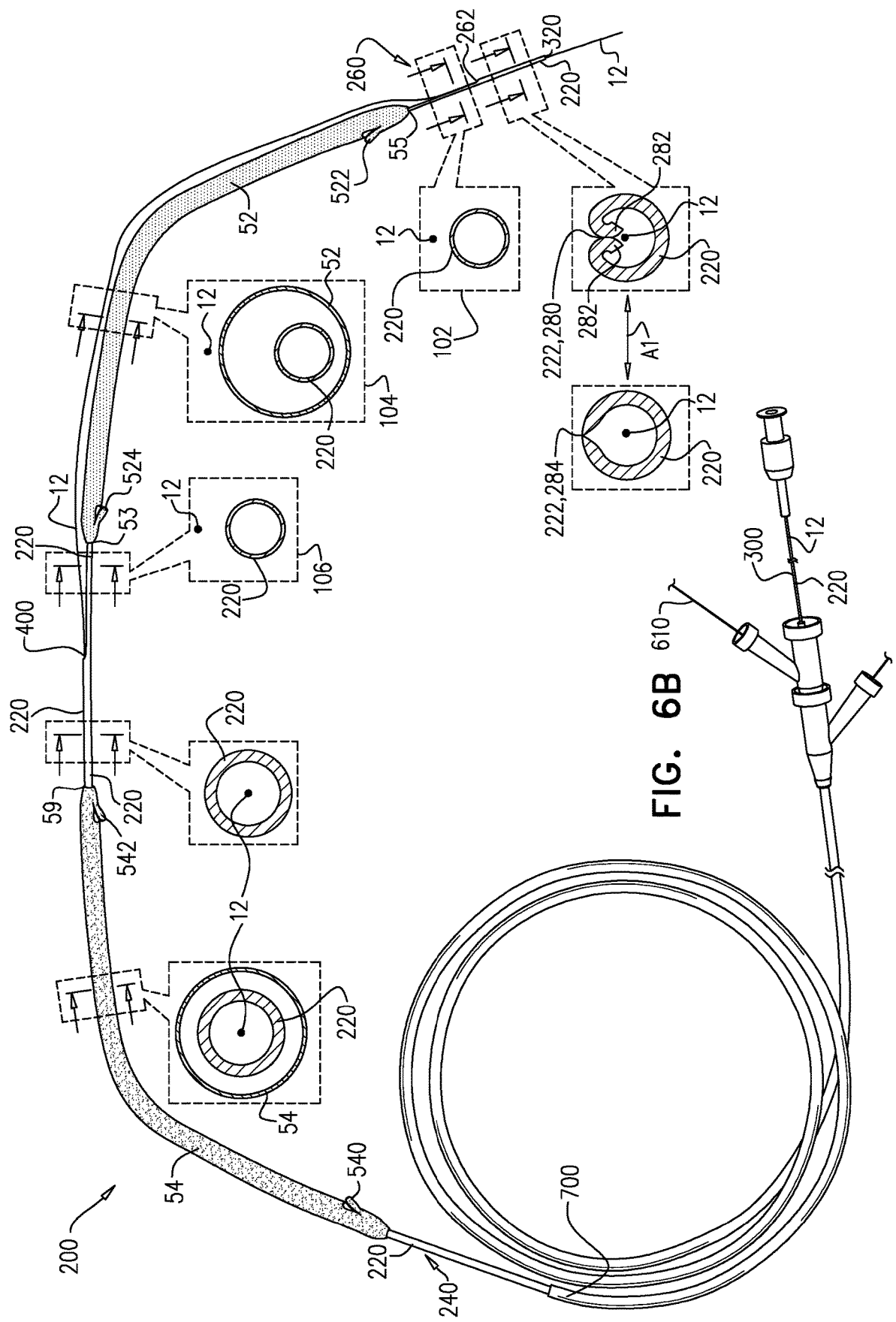

Alternatively, guidewire-engaging portion 222 is shaped to define a weak spot 284, e.g., a splittable portion, configured to tear in response to force applied to weak spot 284 (e.g., by guidewire 12 as shown hereinbelow in FIG. 7B). It is noted that FIGS. 5A and 6A-B show (as indicated by double headed arrow A1) the two options of the guidewire engaging portion 222 being shaped to define either a slit 280 or a weak spot 284. This is by way of illustration and not limitation; it is noted that with respect to FIG. 5B, guidewire engaging portion 222 may be shaped to define slit 280.

Reference is still made to FIGS. 5A-B and 6A-B. As shown, guide tube 220 assumes a collapsed configuration in a portion of guide tube 220 that is typically proximal to guidewire engaging portion 222 and distal to hole 400 (shown in the exploded view in boxes 94, 95, 96 and 97 in FIG. 6A, and in the exploded view in box 98 in FIG. 5A). Alternatively, guide tube 220 may assume varying diameters along a length of the guide tube, e.g., a diameter that is smaller in the portion of guide tube 220 that is typically proximal to guidewire engaging portion 222 and distal to hole 400 (shown in the exploded view in box 100 in FIG. 5B, and in the exploded view in boxes 102, 104, and 106 in FIG. 6B). For some applications, there may be a single portion of the guide tube 220 with a smaller diameter that extends from guidewire engaging portion 222 to hole 400 (such as is shown in FIGS. 6A-B). Alternatively, for some applications, the diameter of guide tube 220 may be smaller in two separate portions of guide tube 220: (i) in a vicinity of guidewire engaging portion 222, proximal to guidewire engaging portion 222, and (ii) in a vicinity of hole 400, distal to hole 400. In between these two portions, guide tube 220 may assume its larger diameter. Alternatively, for some applications, guide tube 220 may have a substantially constant diameter along substantially the entire length of guide tube 220. Typically, guide tube 220 is configured for use with guidewire 12, and the collapsed, or the varying diameter configurations of guide tube 220, allow the guidewire to generally pass in and out of a lumen of guide tube 220.

Reference is still made to FIGS. 5A-B and 6A-B. FIGS. 6A-B are schematic illustrations of apparatus 200 for delivery and deployment of a first stent 52 and a second stent 54 in a lumen of a subject, in accordance with some applications of the present invention.

As shown, apparatus 200 comprises guide tube 220 (as described hereinabove with reference to FIGS. 5A-B and 6A-B), and first and second stents 52 and 54 respectively. As shown, first and second stents 52 and 54 surround guide tube 220, second stent 54 being disposed proximally to first stent 52 and surrounding proximal portion 240 of guide tube 220. First stent 52 is typically disposed over guide tube 220 such that a distal end 55 of first stent 52 is disposed proximally to proximal end 262 of guidewire-engaging portion 222, and proximal end 53 of first stent 52 is disposed distally to hole 400.

Typically, a distal end 59 of second stent 54 is disposed proximally to first stent 52 and proximally to hole 400.

First stent 52 is slidably deployable off of distal end 320 of guide tube 220. Additionally, second stent 54 is also shaped and sized to be advanceable over guide tube 220, typically subsequently to deployment of first stent 52 off of distal end 320 of guide tube 220. Apparatus 200 is typically advanced into a lumen of the subject, and guide tube 220 facilitates placement of first and second stents 52 and 54 within the lumen of the subject.

Reference is now made to FIGS. 7A-H, which depict a general overview of a method for use of apparatus 200 for deploying first and second stents 52 and 54 in a lumen of a subject, in accordance with some applications of the present invention. Typically, stents 52 and 54 are deployed in the lumen of the subject, e.g., a common bile duct of the subject, in order to manage strictures of the lumen. In accordance with some applications of the present invention, similarly to apparatus 20, apparatus 200 is configured such that first stent 52 is advanced into the lumen of the subject against guidewire 12, and second stent 54 is advanced into the lumen over guidewire 12 (i.e., surrounding the guidewire), as shown.

Figure 7A:
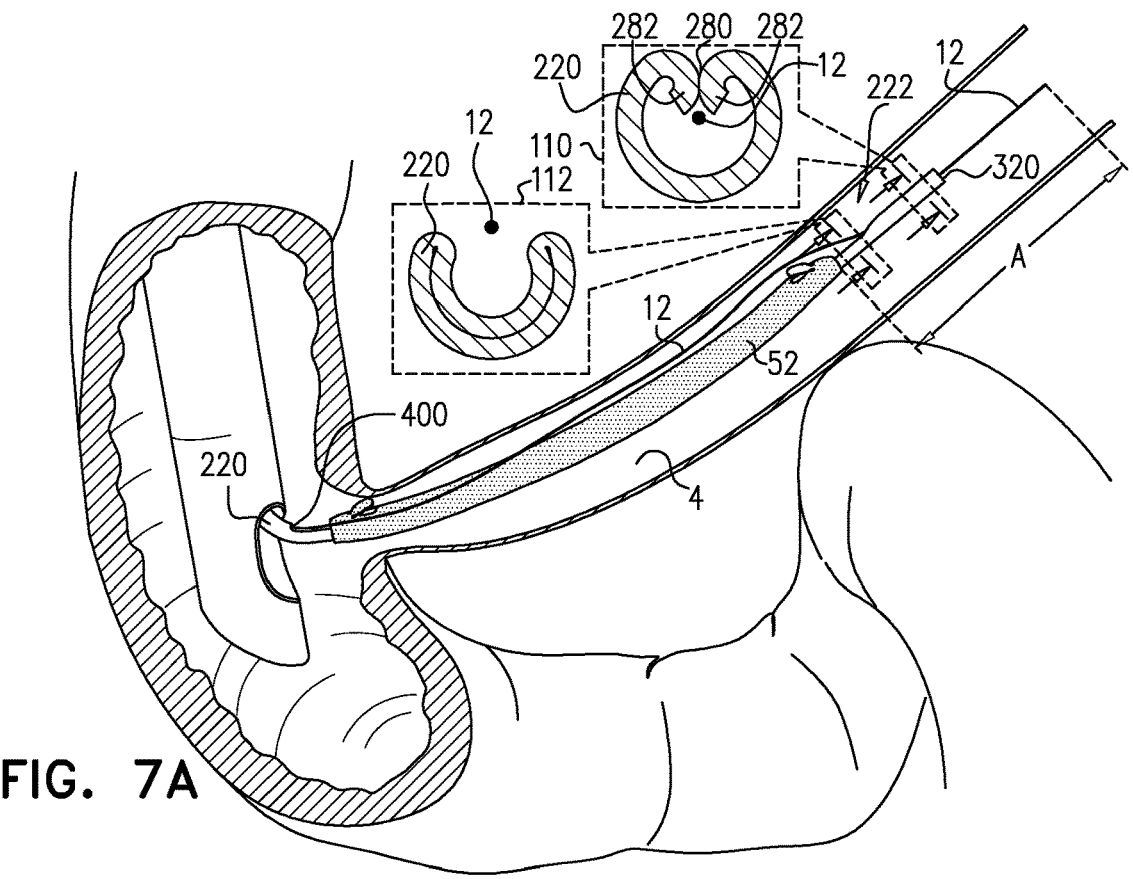
FIGS. 7A-H are schematic illustrations depicting a general overview of a method for deploying first and second stents in a lumen of a subject, in accordance with some applications of the present invention.

Reference is first made to FIG. 7A. In accordance with some applications of the present invention, apparatus 200 (comprising guide tube 220 and first and second stents 52 and 54, as described hereinabove with reference to FIGS. 5A-B and 6A-B) is used in combination with a guidewire 12 to deploy stents 52 and 54 such that they are placed alongside each other in the lumen. Guidewire 12 is typically threaded through guide tube 220 such that following the threading:

(a) guidewire 12 enters a lumen of guide tube 220 from a distal-end 320 opening of guide tube 220, (b) guidewire 12 passes out of the lumen of guide tube 220 at guidewire-engaging portion 222 and disposed against an outer surface of first stent 52, (c) first stent 52 is constrained from distal motion past guidewire-engaging portion 222 of guide tube 220, due to guidewire 12 being disposed in guidewire-engaging portion 222, (d) guidewire 12 passes into the lumen of guide tube 220 through hole 400 proximally to first stent 52, such that guidewire 12 is surrounded by guide tube 220 and second stent 54, and (e) first stent 52 is constrained from proximal motion past hole 400, when guidewire 12 is disposed within hole 400.

It is noted that the exploded view in box 110 in FIG. 7A only shows guidewire engaging portion 222 being shaped to define a slit 280. This is by way of illustration and not limitation; alternatively, guidewire engaging portion 222 may be shaped to define weak spot 284. Similarly, it is noted that the exploded view in box 112 in FIG. 7A only shows the collapsed configuration of the portion of guide tube 220 proximally to guidewire engaging portion 222. Alternatively, this portion of guide tube 220 may utilize the varying diameter configuration as shown in FIGS. 5B and 6B.

Following threading of guidewire 12 through guide tube 220 as described hereinabove, apparatus 200 is advanced into a body of the subject, e.g., into the small intestine, and into lumen 4 of the common bile duct, as shown in FIG. 7A. As shown, first stent 52 is advanced distally over guide tube 220 and against guidewire 12 (i.e., an outer surface of first stent 52 is disposed against guidewire 12). Due to threading of guidewire 12 as described hereinabove, stent 52 is advanced distally in lumen 4 while it is constrained from distal motion guidewire-engaging portion 222. Constrained motion of stent 52 typically allows for stent 52 to be advanced to a desired deployment site within lumen 4 in a controlled manner (i.e., inhibiting uncontrolled distal motion of stent 52, thus allowing the physician to safely perform the implantation at the desired deployment site).

Additionally, due to guidewire 12 being disposed in hole 400, first stent 52 is constrained from proximal motion past hole 400, allowing the physician to advance stent 52 in a controlled manner.

Reference is now made to FIGS. 7B-H.

Figure 7B:
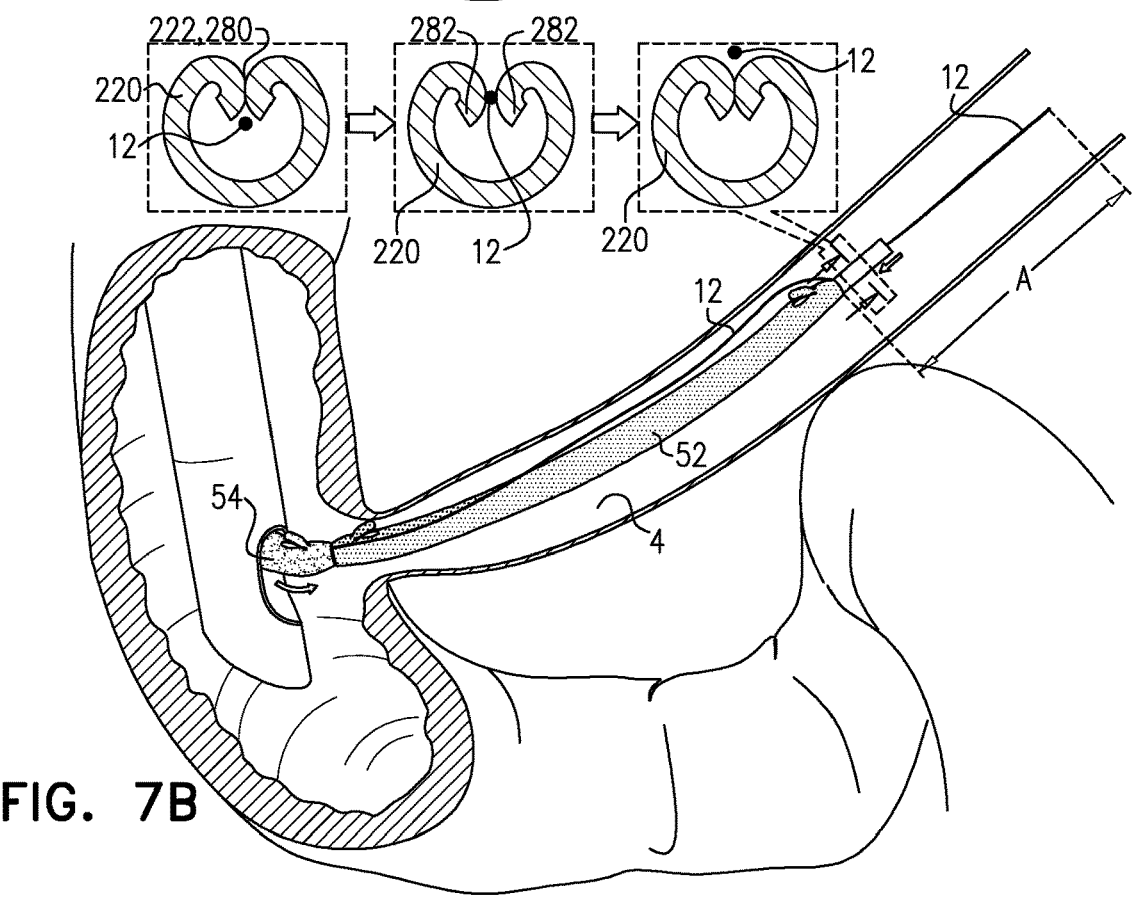

When first stent 52 reaches a desired deployment site within lumen 4, guidewire 12 passes through, i.e., exits, guidewire-engaging portion 222 of guide tube 220, typically by pulling guide tube 220 proximally, causing lateral exiting of guidewire 12 through guidewire-engaging portion 222, as shown in FIG. 7B. Guidewire 12 is shown exiting the lumen of guide tube 220 at guidewire-engaging portion 222 by passing out of slit-lips 282. It is noted that guidewire-engaging portion 222 is shown as a slit by way of illustration and not limitation. For some applications, guidewire-engaging portion 222 is shaped to define a weak spot 284 as described herein with reference to FIGS. 5A-B and 6A-B, and guidewire 12 passes out of the lumen of the guide tube by tearing the weak spot.

As shown in FIG. 7B, guidewire 12 laterally exits guidewire-engaging portion 222 without being advanced distally or proximally. (This is in contrast to the application described in FIGS. 3B and 3C in which guidewire 12 is removed from the guidewire-engaging portion in the distal portion of the guide tube, by pulling guidewire 12 proximally in the direction indicated by arrow 11, shown in FIG. 3B. Guidewire 12 is then typically advanced distally in lumen 4 as indicated by arrow 13 (shown in FIG. 3C) in order to facilitated subsequent deployment of stent 52.) As shown in FIG. 7B, guidewire-engaging portion 222 is arranged to allow passing guidewire 12 out of the guidewire-engaging portion 222 without the need to pull the guidewire proximally to release the guidewire from the guide tube. Instead, guidewire 12 "pops out" of guidewire-engaging portion 222 in a lateral direction, e.g., in response to guide tube 220 being pulled back proximally.

It is additionally noted with respect to FIG. 7B, that in accordance with some applications of the present invention, there is a fixed distance of at least 1 mm and/or less than 80 mm (e.g., 1-80 mm) between first stent 52 and second stent 54 (not shown in FIG. 7B) due to locking of second stent 54 such that it is prevented from distal motion, prior to deployment of first stent 52. An example of such a locking mechanism is described hereinbelow with reference to FIGS. 9A-D. For some applications, the fixed distance is at least 5 mm, and for some applications, the fixed distance is less than 25 mm.

Figure 7C:
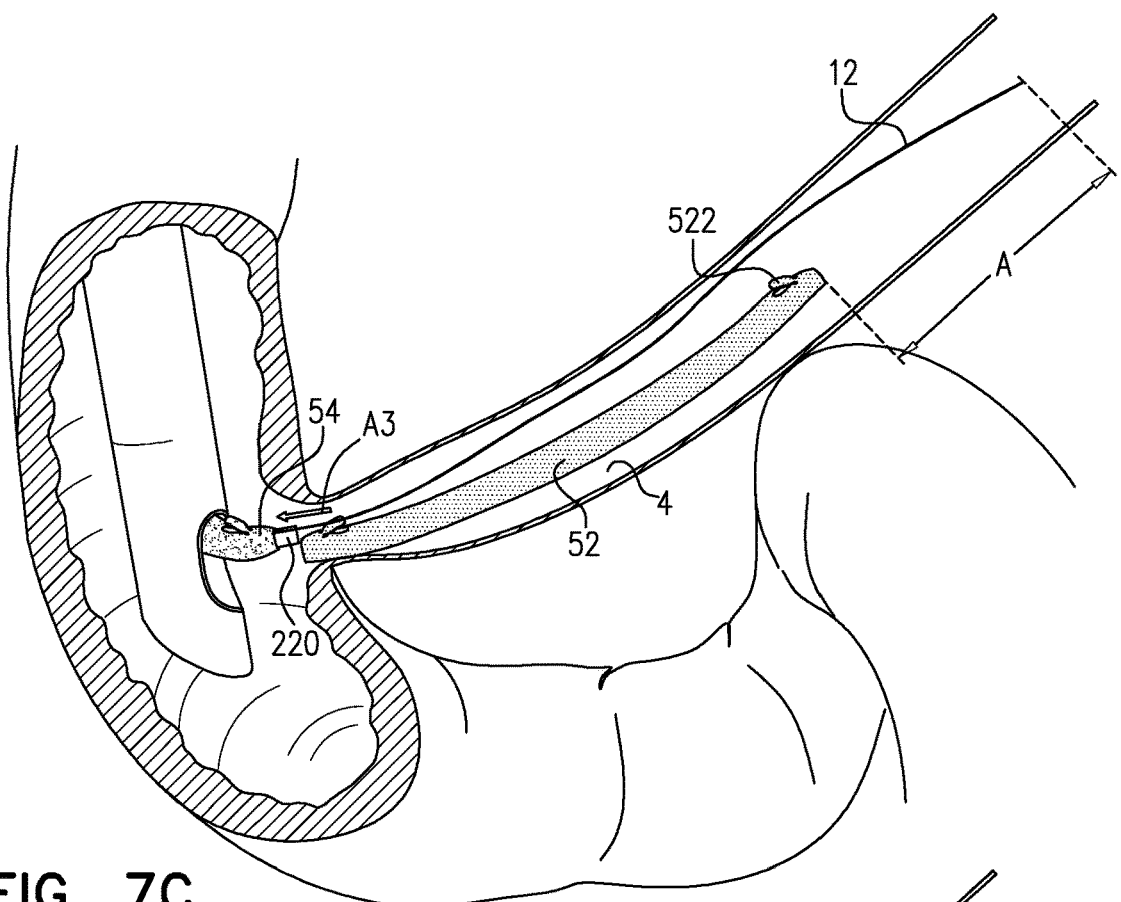

Reference is made to FIG. 7C. Following removal of guidewire 12 from guidewire-engaging portion 222, guidewire 12 is maintained within lumen 4 and is not advanced proximally or distally in the lumen. Removal of guidewire 12 from guidewire-engaging portion 222, as shown in FIG. 7B, typically allows subsequent deployment of first stent 52, by guide tube 220 being withdrawn proximally. In particular, guide tube 220 is typically pulled proximally in the direction indicated by arrow A3 until guide tube 220 is removed from stent 52, and stent 52 is thereby deployed in lumen 4. It is noted that during deployment of first stent 52, guidewire 12 is maintained within lumen 4 and is not advanced proximally or distally in the lumen.

Figure 7D:
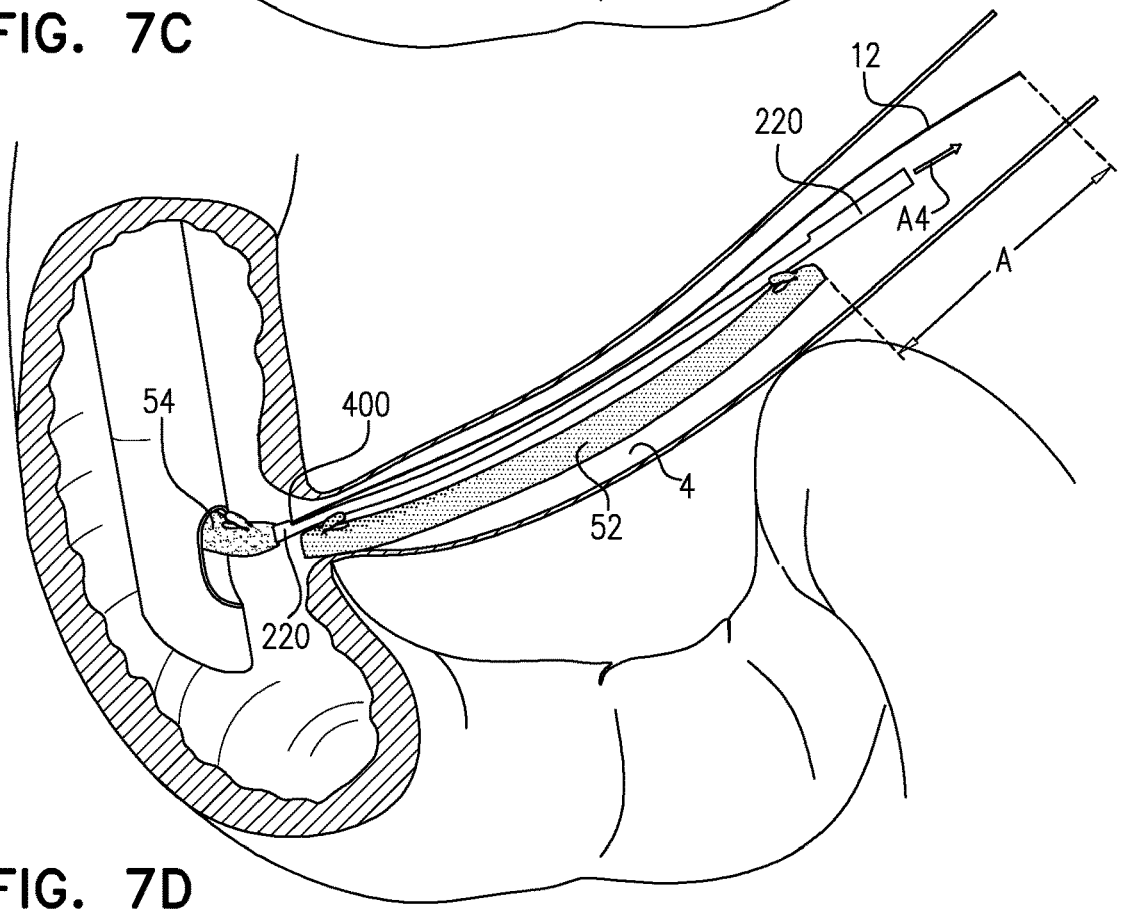
Figure 7E:
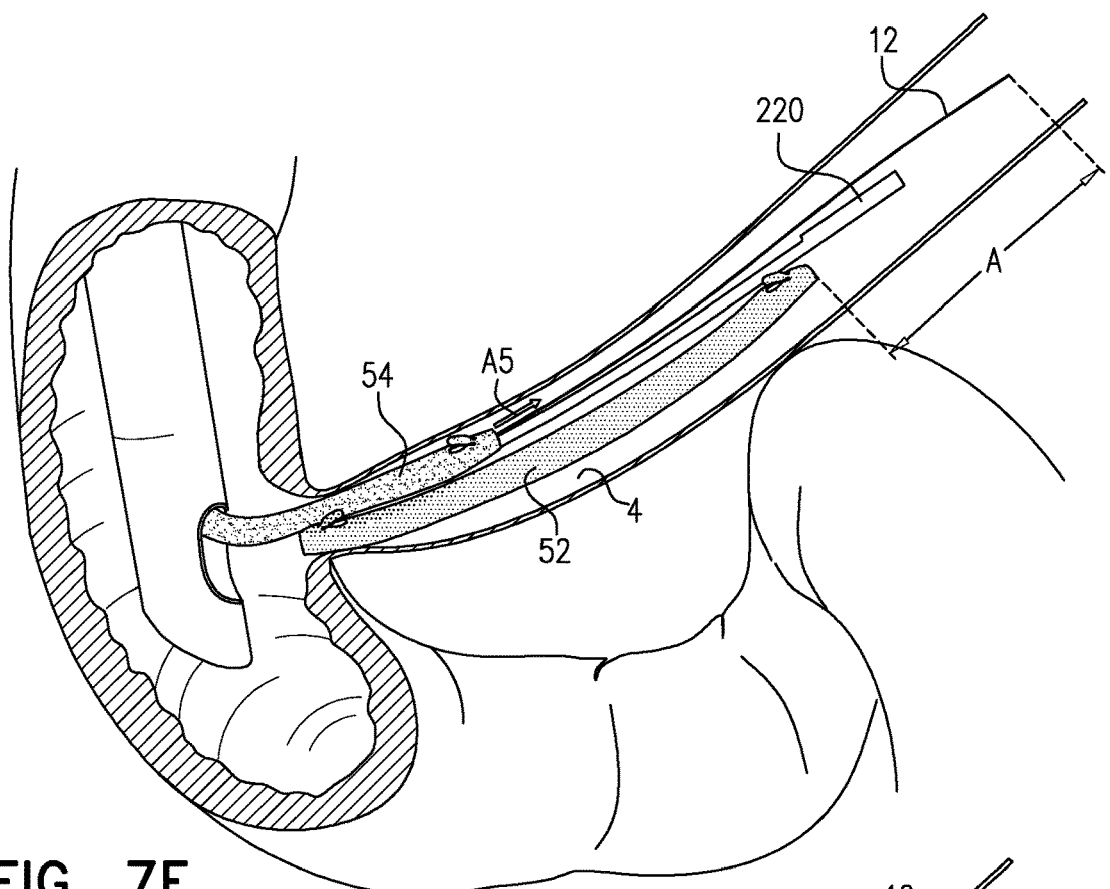
Figure 7F:
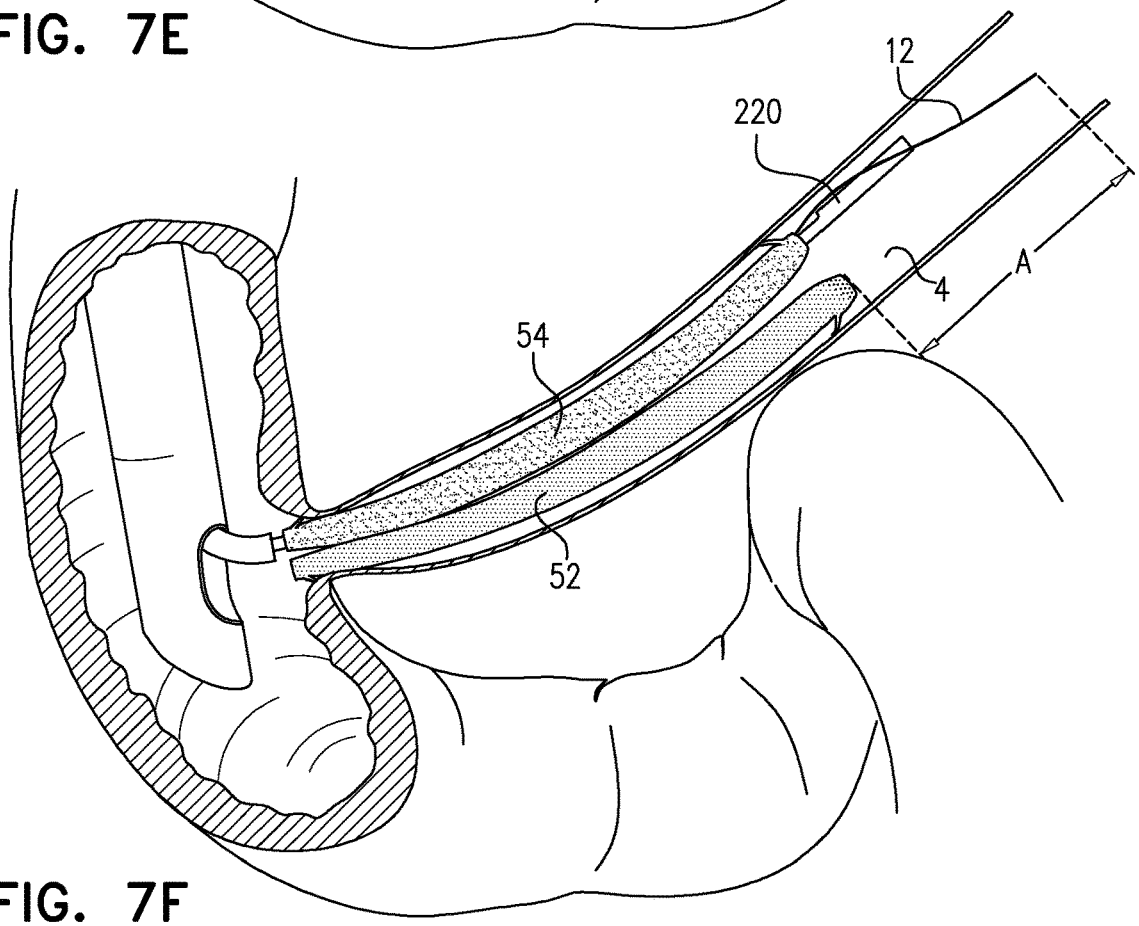

Subsequently to deployment of first stent 52, second stent 54 is advanced over guide tube 220 and over guidewire 12. Optionally, guide tube 220 is advanced distally in the direction indicated by arrow A4 (FIG. 7D). Second stent 54 is advanced distally as indicted by arrow A5 in lumen 4, over guide tube 220 and over guidewire 12 (which is in the lumen of guide tube 220), as shown in FIGS. 7E-F. It is noted that during deployment of second stent 54, guidewire 12 is maintained within lumen 4 and is not advanced proximally or distally in the lumen.

Figure 7G:
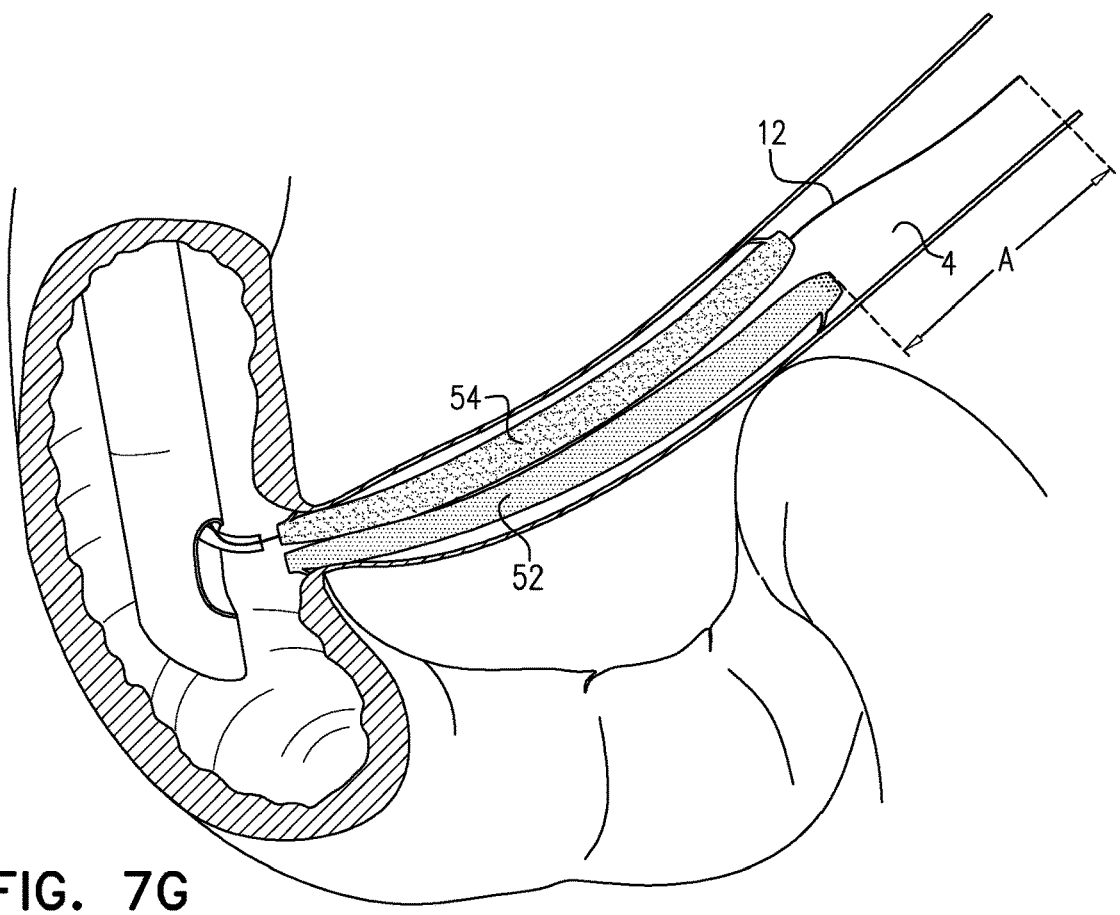
Figure 7H:
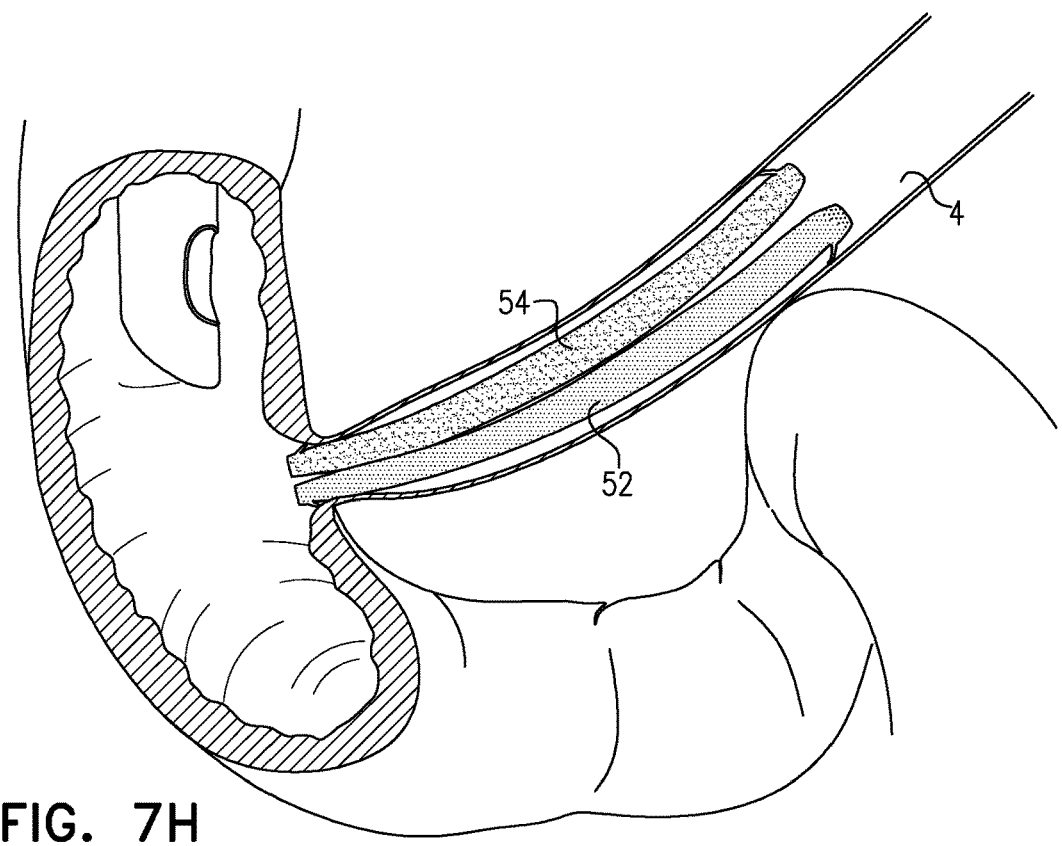

As shown in FIG. 7F, second stent 54 continues to be distally advanced in lumen 4 until a desired deployment site is reached alongside first stent 52. Once second stent 54 is disposed alongside first stent 52 (FIG. 7F), guidewire 12 (and guide tube 22, if present) is retracted by being pulled in a proximal direction and out of the body of the subject, as shown in FIGS. 7G-H.

As shown in FIGS. 7A-H, use of apparatus 200 in accordance with some applications of the present invention, allows for deployment of second stent 54 subsequently to deployment of first stent 52, while maintaining guidewire 12 in a generally constant location within lumen 4. Additionally, apparatus 200 allows for deployment of second stent 54 subsequently to deployment of first stent 52, without removing apparatus 200 from the body of the subject following deployment of first stent 52 in order to mount second stent 54. Notably, first and second stents 52 and 54 are typically mounted at the same time on guide tube 220 (as shown in FIGS. 6A-B) when advanced into the subject's body, to be deployed within the lumen using the techniques described herein.

Reference is now made to FIGS. 8A-B and 9A-D, which are schematic illustrations of locking mechanisms configured to prevent motion of first stent 52 and second stent 54 with respect to the guide tube. The locking mechanisms are typically employed in order to allow first and second stents 52 and 54 to be advanced together over the guide tube in a controlled manner within the lumen of the subject. Once the physician removes each locking mechanism, the respective stent can be deployed off the distal end of the guide tube in the lumen. It is noted that the locking mechanisms described herein with reference to FIGS. 8A-B and 9A-D, may be applied to stent 52 and second stent 54 and guide tubes 22 and 220 shown in FIGS. 1-7H. FIGS. 8A-B and 9A-D refer to guide tube 220 by way of illustration and not limitation. It is to be understood that the locking mechanisms described with reference to FIGS. 8A-B and 9A-D may also be used with guide tube 22.

Reference is first made to a first lock 600 for preventing proximal and distal motion of first stent 52 with respect to guide tube 220, as illustrated in FIGS. 8A-B, 9A, and 9D. Typically, first lock 600 is configured to prevent proximal motion of first stent 52 past a location that is at least 1-80 mm (e.g., 2-80 mm, e.g., 5-80 mm, e.g., 5-25 mm) distal to distal end 59 of second stent 54. Additionally, first lock 600 is configured to prevent distal motion of stent 52, such that stent 52 does not slip off the distal end of guide tube 220 while it is being advanced in the lumen of the subject until a desired implantation location is reached, and the physician removes first lock 600.

Typically, first lock 600 comprises a first locking wire 610 and a locking loop 620.

Figure 9A:
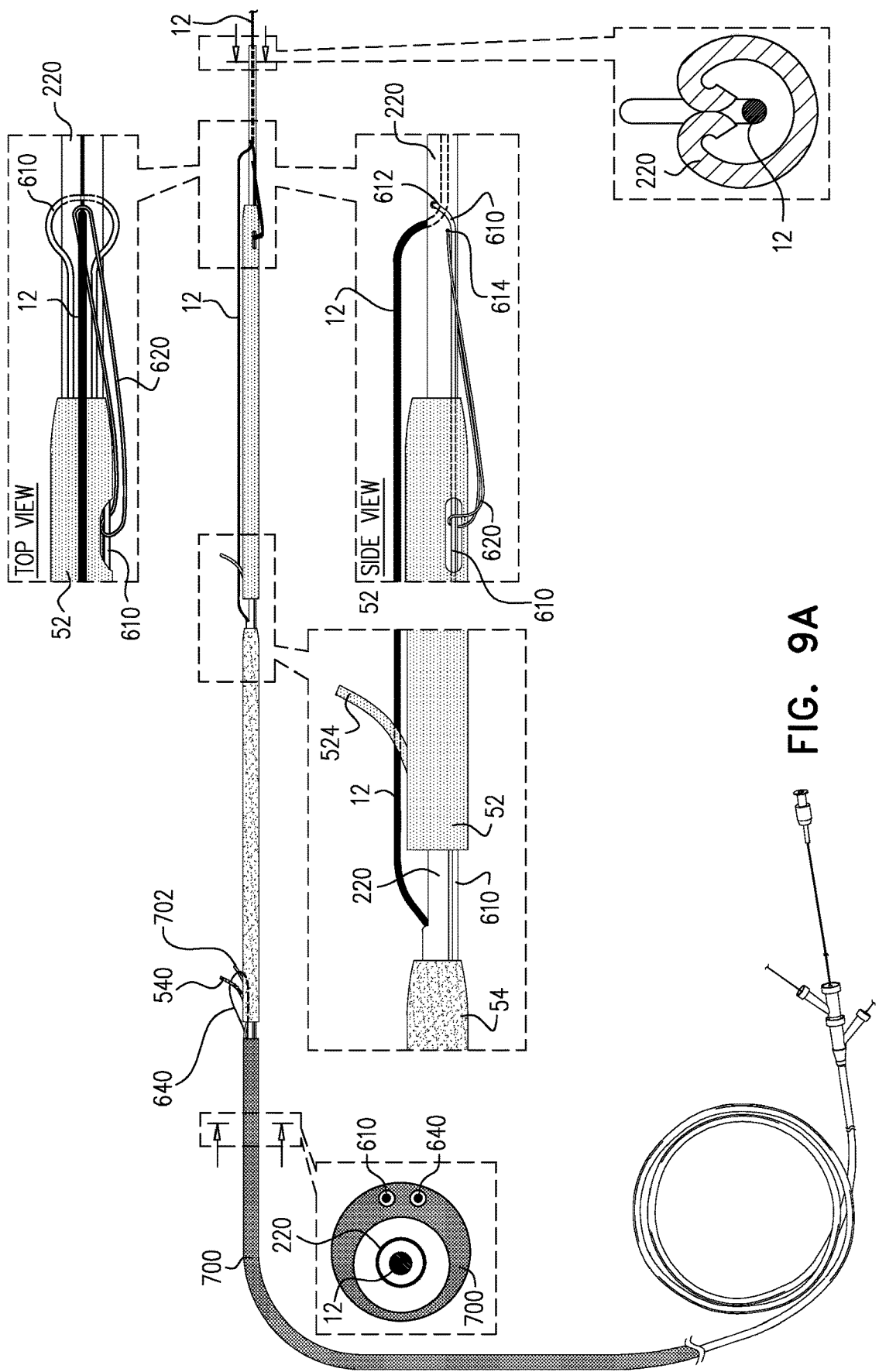
FIGS. 9A-D are schematic illustrations of locking mechanisms comprising first and second locks configured to prevent motion of the first stent and the second stent, respectively, with respect to the guide tube.
Figure 9B:
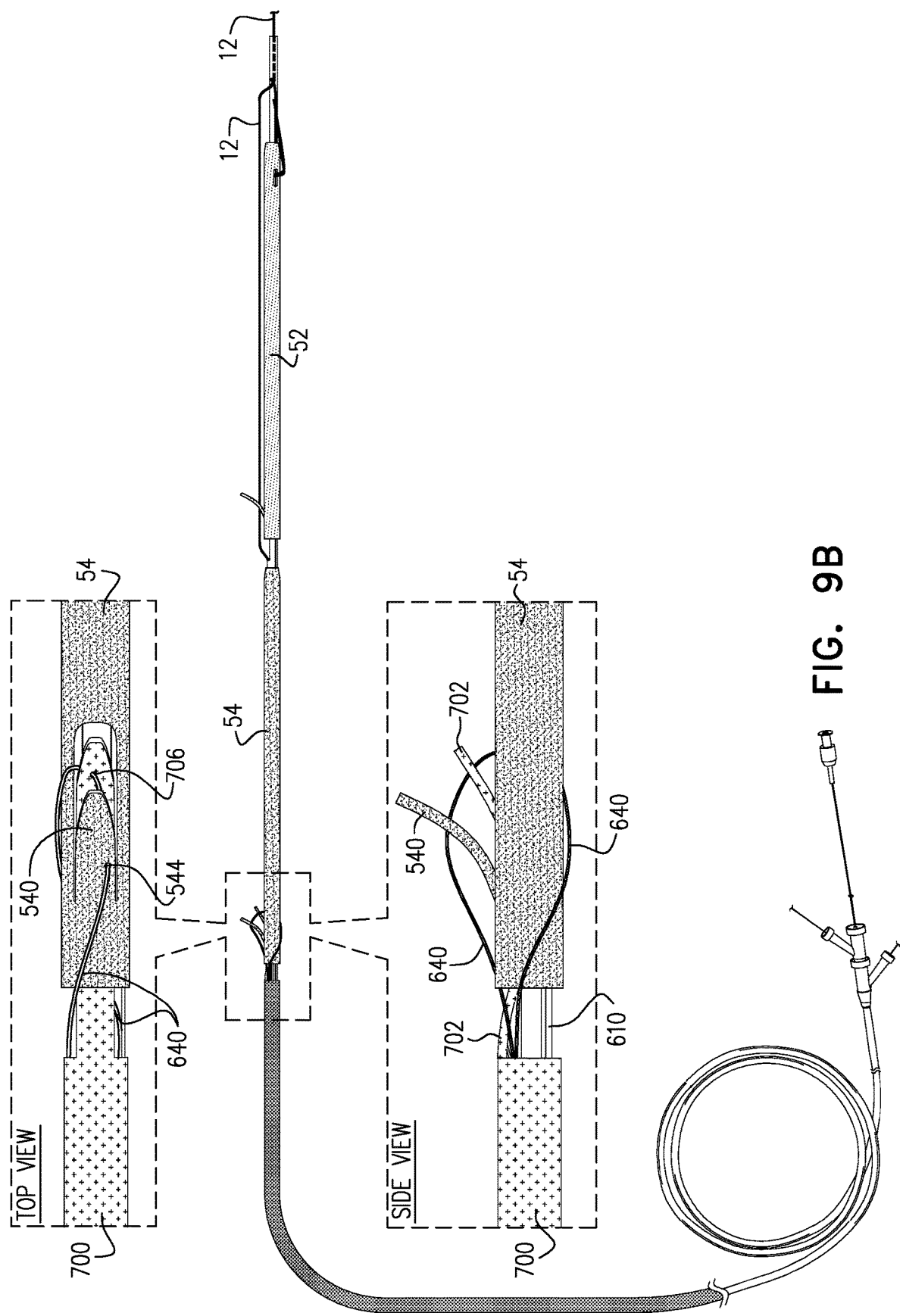
Figure 9C:
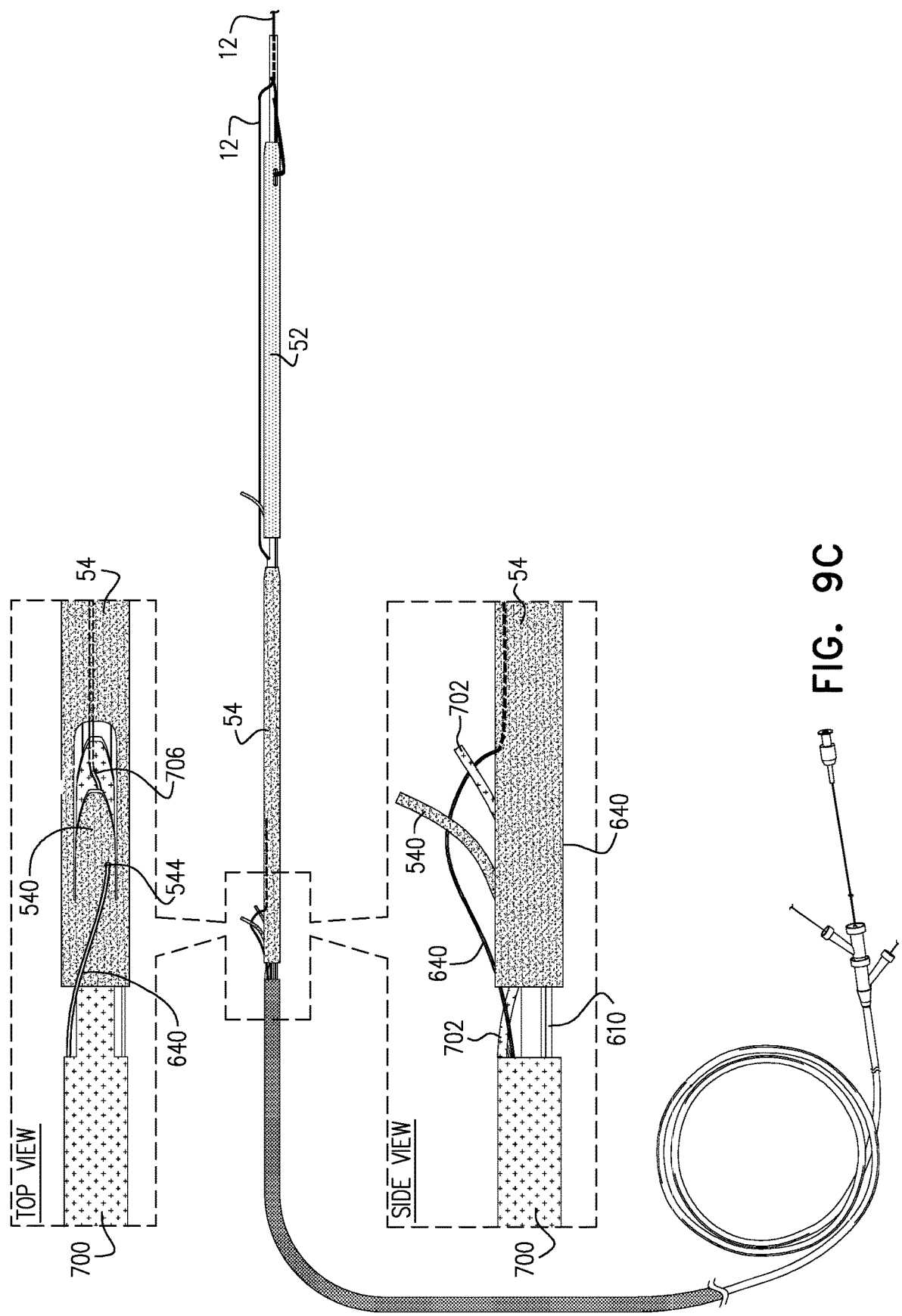
Figure 9D:
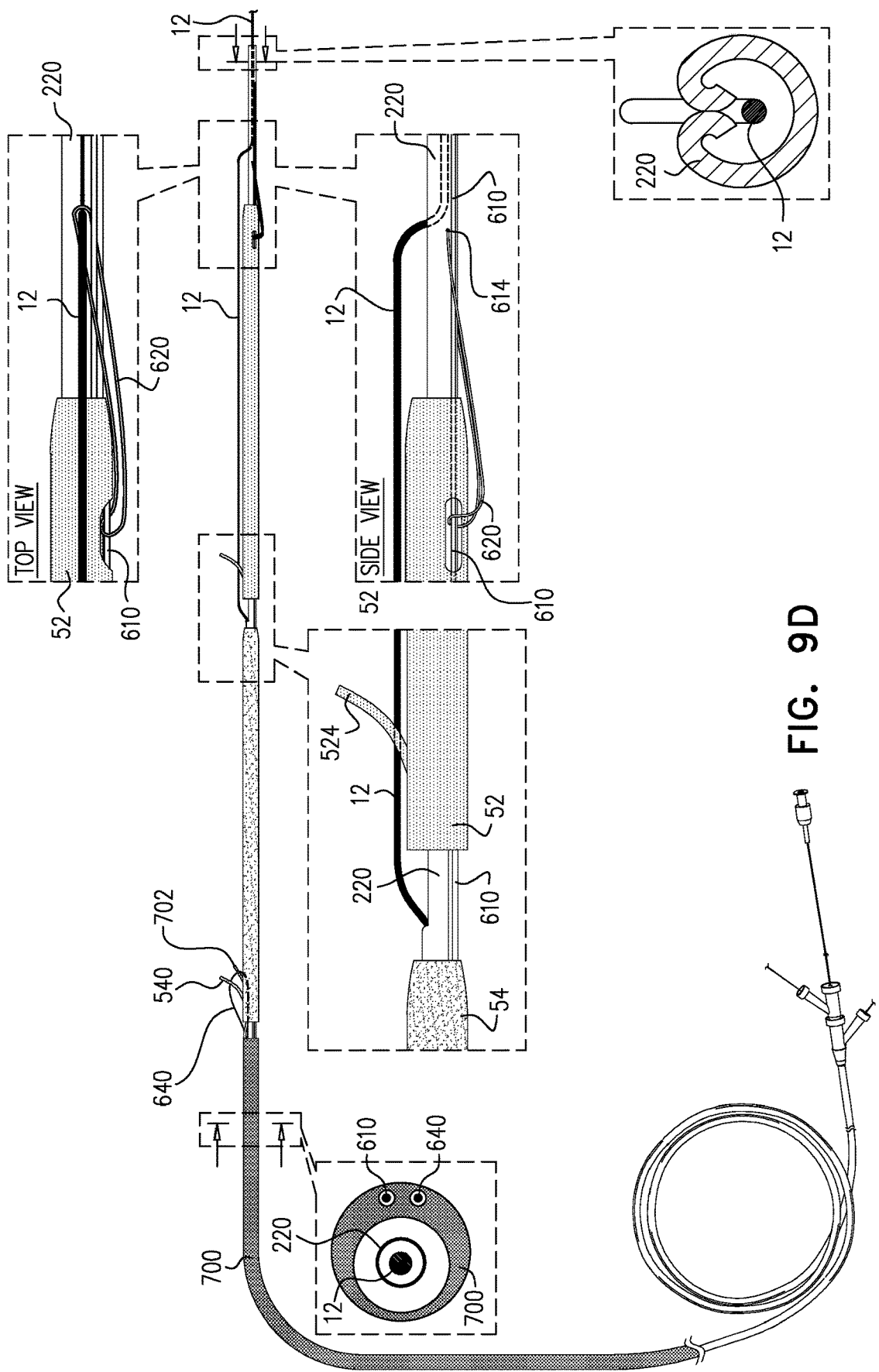

Locking loop 620 is typically secured to guide tube 220 by the loop being looped through two lateral holes 614 in guide tube 220 (FIGS. 9A and 9D).

First locking wire 610 typically comprises a thin metal wire having a diameter of 0.1-0.35 mm, e.g., 0.2 mm. First locking wire 610 typically runs from the proximal portion of apparatus 200 between guide tube 220 and an inner surface of first and second stents 52 and 54, and is threaded through locking loop 620 (typically being accessed by locking loop 620 via a hole in the wall of first stent 52).

Figure 8A:
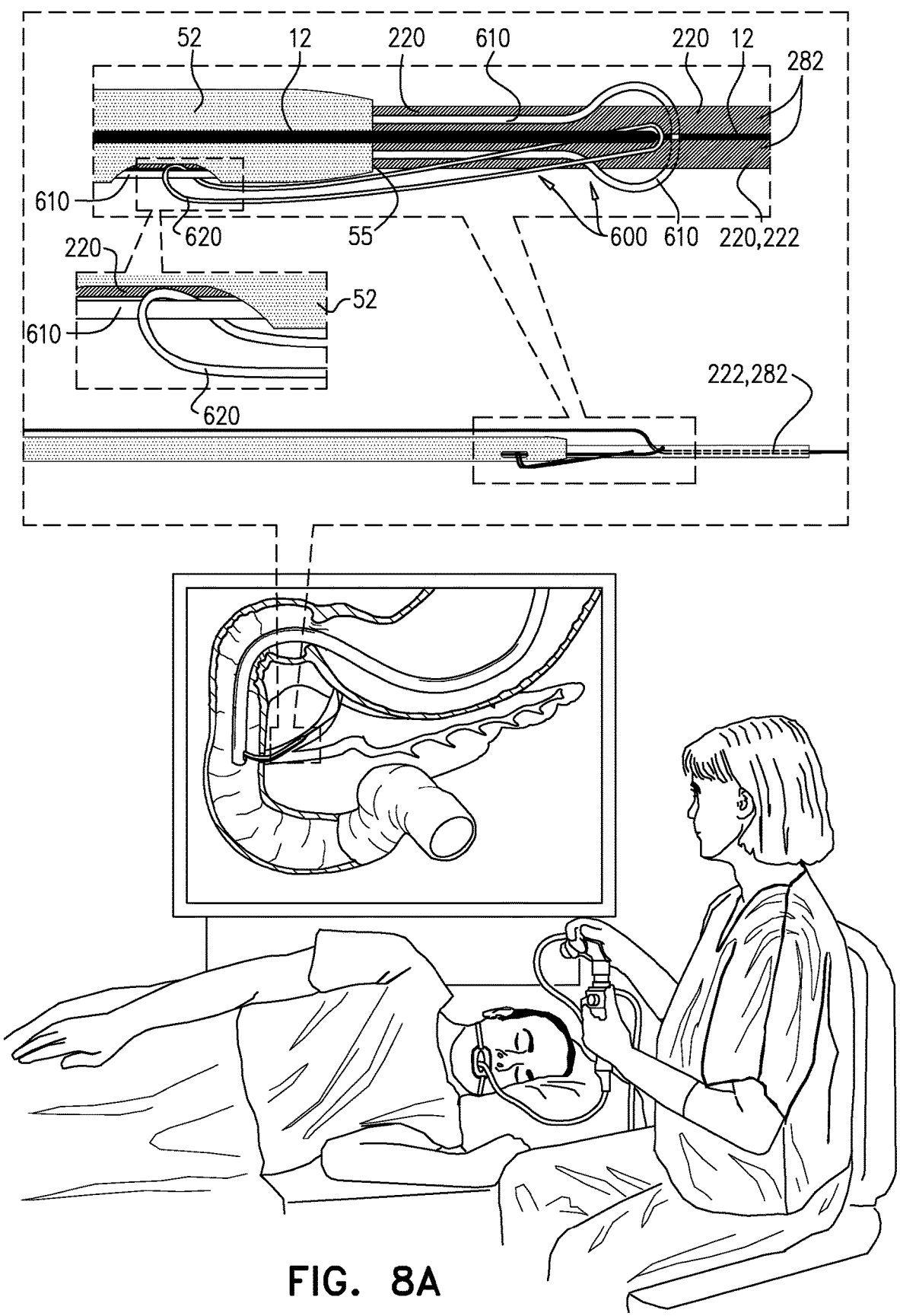
FIGS. 8A-B are schematic illustrations of a locking mechanism comprising a lock configured to prevent motion of the first stent with respect to the guide tube.

First locking wire 610 exits first stent 52 through distal end 55 of stent 52 and is disposed adjacent to the side of guide tube 220 distal to distal end 55. For some applications, such as is shown in FIGS. 8A and 9A, locking wire 610 passes through a lateral hole 612 in the side of guide tube 220, travels across guide tube 220, and leaves guide tube 220 via an additional lateral hole 612 in the opposite side. Locking wire 610 then runs proximally along the inner surface of first stent 52, outside of guide tube 220. This locks first stent 52 in place and prevents distal or proximal motion of the stent. Additionally, when first locking wire 610 passes through lateral holes 612, slit lips 282 are brought in contact with each other, to maintain slit 280 in a closed state.

Figure 8B:
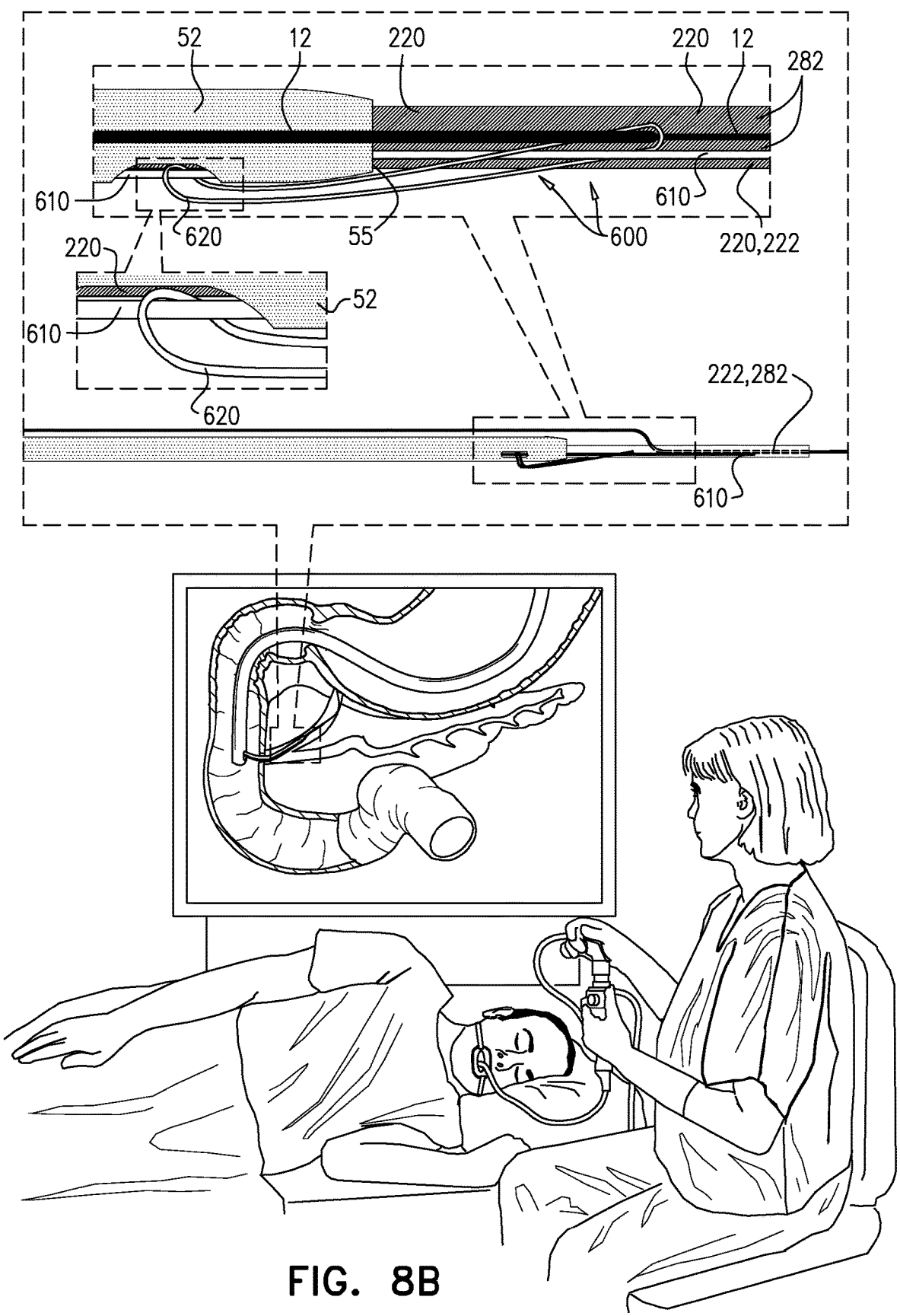

Alternatively, such as is shown in FIGS. 8B and 9D, after locking wire 610 is threaded through locking loop 620, locking wire 610 continues to run distally outside of guide tube 220.

Once stent 52 is in the desired location in the lumen of the subject, the physician pulls first locking wire 610 proximally, thereby releasing the locking of first stent 52 by disengaging locking wire 610 from locking loop 620. This disengaging allows proximal motion of guide tube 220, whereby first stent 52 is deployed distally off guide tube 220. It is noted that distal flap 542 of first stent 52 is not shown in FIGS. 8A-B and 9A-D for clarity.)

Reference is now made to a second lock comprising locking wire 640 for preventing distal motion of second stent 54 with respect to guide tube 220, as illustrated in FIGS. 9B-C.

As shown in FIG. 9B, for some applications, second stent 54 is shaped to define a hole 544 in a portion of second stent 54 (e.g., in flap 540). Additionally, a pusher tube 700 disposed proximally to second stent 54 and configured to push second stent 54 off of guide tube 220, is shaped to define a hole 706 in a portion of the pushing tube (e.g., in a distal extension portion 702 of the pushing tube).

Second locking wire 640 passes through the hole 544 in the portion of second stent 54 and through hole 706 in the portion 702 of pusher tube 700 to prevent distal motion of stent 54. Subsequently to deployment of first stent 52, second locking wire 640 is removed from holes 544 and 706, releasing second stent 54 from being locked. Subsequently, second stent 54 is deployed off the distal end of guide tube 220.

For some applications, such as is shown in FIG. 9B, after passing through holes 544 and 706, second locking wire 640 loops back towards pusher tube 700, and then runs proximally along the inner surface of pusher tube 700, outside of guide tube 220.

Alternatively, for some applications, such as is shown in FIG. 9C, after passing through holes 544 and 706, second locking wire 640 continues to run distally along the inner surface of second stent 54, outside of guide tube 220.

Reference is still made to FIGS. 8A-B and 9A-D. it is noted that first lock 600 is not arranged to utilize guidewire 12 to prevent distal, or proximal motion of first stent 52. It is additionally noted that locking wire 640 is not arranged to utilize guidewire 12 to prevent distal motion of second stent 54.

In summary of the applications of the present invention described hereinabove with reference to FIGS. 8A-B and 9A-D, first and second stents 52 and 54 are both locked to guide tube 220 pre-procedurally, i.e., before insertion of guide tube 220 into the subject's body.

Reference is made to FIGS. 9A and 9D. For some applications, locking wires 610 and 640 are disposed in respective lumens in a wall of pusher tube 700.

Reference is made to FIGS. 1-9D. It is noted that for some applications, apparatus 20 and 200 are configured to deploy more than two stents, e.g., three or four stents, in the lumen of the subject (configuration not shown).

Reference is still made to FIGS. 1-9D. It is noted that apparatus 20 and 200 are described with reference to lumen 4 of a common bile duct by way of illustration and not limitation. The scope of the present invention includes use of apparatus 20 and 200 in any suitable lumen to deploy multiple stents, tubes, or other apparatus in the lumen. For example, techniques and apparatus described herein may be used in a urethra, and/or in a ureter, and/or in a pancreatic duct, and/or in an esophagus, and/or in a trachea of the subject. Additionally, or alternatively, techniques and apparatus described herein may be used to deploy two or more prostatic stents.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
    a guide tube shaped to define a guidewire-engaging portion at a distal portion of the guide tube, a proximal end of the guidewire-engaging portion being located distally to a proximal end of the guide tube;
    a first stent surrounding the guide tube so as to be advanceable together with the guide tube into a lumen of a subject, the first stent being slidable along the guide tube such that a distal end of the first stent is disposed proximally to the guidewire-engaging portion of the guide tube;
    a guidewire arranged (i) entering a lumen of the guide tube from a distal-end opening of the guide tube, (ii) disposed in the guidewire-engaging portion, and (iii) passing out of the lumen of the guide tube proximally to the guidewire-engaging portion of the guide tube, such that the first stent is constrained from distal motion past the guidewire-engaging portion by the guidewire being disposed within the guidewire-engaging portion; and
    a second stent, proximal to the first stent, surrounding a proximal portion of the guide tube and the guidewire, and shaped and sized to be advanceable along the guide tube, and
    wherein:
    (i) the guidewire is positioned to laterally exit the guidewire-engaging portion without being advanced distally or proximally,
    (ii) the first stent is slidably deployable off of a distal end of the guide tube upon the guidewire having exited the guidewire-engaging portion, without the guidewire having been moved proximally subsequent to the guidewire exiting the guidewire-engaging portion, and
    (iii) the second stent is slidably deployable off of the distal end of the guide tube and placeable alongside the first stent subsequently to deployment of the first stent off of the distal end of the guide tube, without the guidewire having been moved proximally subsequent to the guidewire exiting the guidewire-engaging portion.

2. The apparatus according to claim 1, wherein the first stent (a) has an outer surface disposed against the guidewire and (b) is configured to be advanced into the lumen of the subject while the outer surface is disposed against the guidewire.

3. The apparatus according to claim 1, wherein the guidewire-engaging portion is shaped to define a slit extending proximally along a wall of the guide tube, from the distal end of the guide tube, the slit having a length of 1-70 mm.

4. The apparatus according to claim 3, wherein the slit is shaped to define two slit lips that are in contact with each other to define a closed-slit configuration in the absence of any forces applied to the slit lips, and disengageable from each other, by application of a force to the lips, to define an opened-slit configuration.

5. The apparatus according to claim 3,
    wherein the slit is shaped to define two slit lips that are in contact with each other to define a closed-slit configuration, and disengageable from each other to define an opened-slit configuration, and
    further comprising a lock which:
    presses the slit lips against each other in the closed-slit configuration when the guidewire is disposed in the guidewire-engaging portion to inhibit the lateral exiting of the guidewire from the guidewire-engaging portion, and
    allows the lateral exiting of the guidewire from the guidewire-engaging portion in the opened-slit configuration when the lock does not press the slit lips against each other.

* * * * *